(12) United States Patent
Furuhata

(10) Patent No.: US 11,452,432 B2
(45) Date of Patent: Sep. 27, 2022

(54) ENDOSCOPE DEVICE AND METHOD FOR CAUSING STILL IMAGE FILE WITH MEASUREMENT CORRECTION DATA WRITTEN AND MOVING IMAGE FILE TO BE ASSOCIATED WITH EACH OTHER

(71) Applicant: Evident Corporation, Nagano (JP)

(72) Inventor: Tsuyoshi Furuhata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 659 days.

(21) Appl. No.: 16/238,693

(22) Filed: Jan. 3, 2019

(65) Prior Publication Data

US 2019/0133418 A1 May 9, 2019

Related U.S. Application Data

(63) Continuation of application No. PCT/JP2017/023534, filed on Jun. 27, 2017.

(30) Foreign Application Priority Data

Jul. 12, 2016 (JP) .............................. JP2016-137729

(51) Int. Cl.
*A61B 1/00* (2006.01)
*A61B 1/045* (2006.01)
(Continued)

(52) U.S. Cl.
CPC ............ *A61B 1/00009* (2013.01); *A61B 1/00* (2013.01); *A61B 1/0002* (2013.01);
(Continued)

(58) Field of Classification Search
None
See application file for complete search history.

(56) References Cited

U.S. PATENT DOCUMENTS

2003/0060681 A1* 3/2003 Yokota ............... A61B 1/00039
600/117
2009/0158315 A1* 6/2009 Bendall .................. H04N 7/185
725/32
(Continued)

FOREIGN PATENT DOCUMENTS

JP 2009-258427 A 11/2009
JP 2010-167031 A 8/2010
(Continued)

OTHER PUBLICATIONS

International Search Report dated Sep. 26, 2017 issued in PCT/JP2017/023534.

*Primary Examiner* — John P Leubecker
(74) *Attorney, Agent, or Firm* — Scully, Scott, Murphy & Presser, P.C.

(57) ABSTRACT

In an endoscope device, a data reading unit reads measurement correction data corresponding to a type of an optical adapter from a first memory. A still image file generating unit generates a still image file including image data when moving image recording processing is performed. A data writing unit writes the measurement correction data in the still image file. A moving image file generating unit generates a moving image file including the image data when the moving image recording processing is performed. A file recording unit causes the still image file in which the measurement correction data is written, and the moving image file to be associated with each other and to be recorded in a second memory.

14 Claims, 16 Drawing Sheets

(51) Int. Cl.
  *G06T 7/00* (2017.01)
  *A61B 1/04* (2006.01)
  *A61B 1/06* (2006.01)
(52) U.S. Cl.
  CPC ...... *A61B 1/00006* (2013.01); *A61B 1/00039* (2013.01); *A61B 1/00045* (2013.01); *A61B 1/00062* (2013.01); *A61B 1/00096* (2013.01); *A61B 1/00101* (2013.01); *A61B 1/04* (2013.01); *A61B 1/045* (2013.01); *A61B 1/0676* (2013.01); *G06T 7/00* (2013.01)

(56) References Cited

U.S. PATENT DOCUMENTS

| | | | | |
|---|---|---|---|---|
| 2010/0097642 | A1* | 4/2010 | Sumi | H04N 1/2307 358/1.15 |
| 2010/0182413 | A1* | 7/2010 | Numata | A61B 1/00039 348/65 |
| 2010/0315496 | A1* | 12/2010 | Miyayashiki | H04N 7/183 348/65 |
| 2011/0050931 | A1* | 3/2011 | Fujiyama | H04N 5/232939 348/220.1 |
| 2011/0055296 | A1* | 3/2011 | Shimazaki | H04N 1/2112 707/822 |
| 2013/0300888 | A1* | 11/2013 | Kubo | H04N 5/232933 348/220.1 |
| 2014/0002630 | A1* | 1/2014 | Yokota | G01B 11/245 348/82 |
| 2014/0028819 | A1* | 1/2014 | Nakano | A61B 1/00009 348/65 |
| 2015/0022689 | A1* | 1/2015 | Nakase | H04N 5/23245 348/231.2 |
| 2015/0062376 | A1* | 3/2015 | Ohnishi | H04N 1/2129 348/231.2 |

FOREIGN PATENT DOCUMENTS

| | | |
|---|---|---|
| JP | 2010-286765 A | 12/2010 |
| JP | 2014-026217 A | 2/2014 |

* cited by examiner

FIG. 5

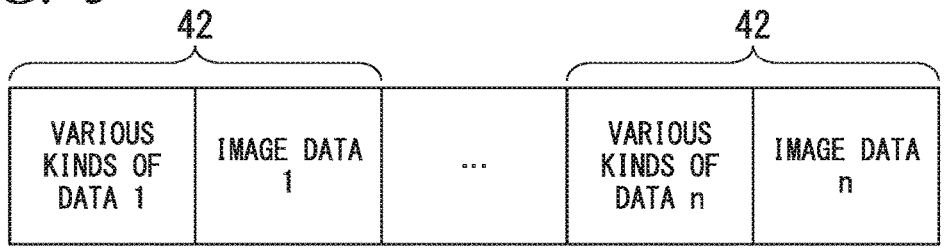

FIG. 6

| TAG | NAME | DEFINITION |
|---|---|---|
| SOI | START OF IMAGE | SOI MARKER (THIS INDICATES THAT REGION TO NEXT MARKER IS DESIGNATED AS IMAGE REGION AND IS SAVED) |
| APP1 | (OMITTED) | USED IN REGION IN WHICH ATTACHMENT INFORMATION FOR IMAGE IS RECORDED |
| TIFF Header | (OMITTED) | REGION FOR STORING HEADER INFORMATION OF TIFF |
| 0th IFD | (OMITTED) | REGION FOR RECORDING ATTACHMENT INFORMATION RELATED TO MAIN IMAGE. ALSO INCLUDES INFORMATION OF 1st IFD |
|  | Date Time Data | DATE AND TIME OF FILMING |
| ExifIFD | (OMITTED) | REGION FOR RECORDING INFORMATION OF CAMERA FILMING |
|  | User Comment Data | REGION FOR USER COMMENTS |
| 1stIFD | (OMITTED) | REGION IN WHICH INFORMATION RELATED TO THUMBNAIL (SAMPLE IMAGE REDUCED IN SIZE) IS REGISTERED |
|  | Xresolution | RESOLUTION OF IMAGE IN WIDTH |
|  | Yresolution | RESOLUTION OF IMAGE IN HEIGHT |
|  | Thumbnail Image Data | THUMBNAIL |
| Makernote | Makernote | ORIGINAL INFORMATION OF FILMING OF MAKER |
| ... | ... | ... |
| COMPRESSED DATA |  | MAIN IMAGE DATA |
| EOI | END OF IMAGE | EOI MARKER |

ENDOSCOPE DEVICE AND METHOD FOR CAUSING STILL IMAGE FILE WITH MEASUREMENT CORRECTION DATA WRITTEN AND MOVING IMAGE FILE TO BE ASSOCIATED WITH EACH OTHER

Priority is claimed on Japanese Patent Application No. 2016-137729, filed Jul. 12, 2016, and the present application is a continuation application based on International Patent Application PCT/JP2017/023534, filed on Jun. 27, 2017, the contents of both Japanese Patent Application and PCT Application are incorporated herein by reference.

BACKGROUND OF THE INVENTION

Field of the Invention

The present invention relates to an endoscope device.

Description of Related Art

Endoscope devices capable of measuring a subject are known. In order to enhance measurement accuracy, measurement is performed on the basis of an image corrected by using measurement correction data. For example, an endoscope device known in the related art includes an optical adapter that has two optical systems. The optical adapter can be mounted at a tip of an endoscope insertion portion, and the optical adapter can be detached from the tip of the endoscope insertion portion. The endoscope device performs matching of two images on the basis of two pieces of image information obtained by performing coordinate transformation of the two images captured via the optical adapter. Accordingly, the endoscope device obtains three-dimensional coordinates of an arbitrary point on a subject.

Characteristics of imaging conditions of an image captured by an endoscope device change in accordance with the state of the endoscope device (for example, the kind of the optical adapter). Therefore, in order to accurately perform measurement, the endoscope device corrects an image on the basis of measurement correction data in accordance with the state of the endoscope device, and measures a subject by using the corrected image.

Convenience of measurement is enhanced by performing measurement on the basis of moving image data. For example, at a site where an inspection is performed, a user inspects a subject by using an endoscope device and images a part intended to be measured. An image of a part which the user intends to measure is recorded in a memory as a still image. In the future, the user performs measurement by using the still image recorded in this memory. However, images that can be used in measurement are only still images captured at an inspection site. When a still image is not suitable for measurement, there is a possibility that measurement accuracy will deteriorate and desired measurement processing will not be able to be performed. Therefore, there is a method in which a user finds an image intended for measurement in a state in which moving image data constituted by a plurality of image frames is reproduced. In this method, a user is more likely to find an image intended for measurement, and convenience of measurement is enhanced.

Japanese Unexamined Patent Application, First Publication No. 2010-286765 and Japanese Unexamined Patent Application, First Publication No. 2010-167031 disclose endoscope devices which have been made in consideration of the foregoing circumstances.

Japanese Unexamined Patent Application, First Publication No. 2010-286765 discloses an endoscope device in which measurement can be performed on the basis of moving image data. Specifically, measurement correction data is applied to only part of image data of a plurality of pieces of image data constituting the moving image data captured by an imaging unit. In Japanese Unexamined Patent Application, First Publication No. 2010-286765, measurement correction data is disclosed as additional data. At the time of measurement, measurement correction data is read from moving image data, and image data of a measurement target is acquired from a plurality of pieces of image data constituting moving image data. This image data is corrected on the basis of the measurement correction data and measurement is performed on the basis of the corrected image data.

Japanese Unexamined Patent Application, First Publication No. 2010-167031 discloses an endoscope device in which measurement can be performed on the basis of moving image data. Specifically, measurement correction data is not saved in image data and is saved in a memory independently from the image data. In Japanese Unexamined Patent Application, First Publication No. 2010-167031, measurement correction data is disclosed as data for correction. The optical adapter type data is added to the moving image data. At the time of measurement, image data of a measurement target is acquired from the moving image data, and measurement correction data corresponding to the optical adapter type data included in the moving image data is read from the memory. The acquired image data is corrected on the basis of the measurement correction data and measurement is performed on the basis of the corrected image data.

SUMMARY OF THE INVENTION

According to a first aspect of the present invention, an endoscope device includes an endoscope insertion portion, an adapter type determining unit, an imaging unit, a data reading unit, a still image file generating unit, a data writing unit, a moving image file generating unit, and a file recording unit. The adapter type determining unit determines a type of an optical adapter for measurement mounted at a tip of the endoscope insertion portion. The imaging unit images a subject and generates an image of the subject. The data reading unit reads measurement correction data corresponding to the type of the optical adapter from a first memory. The measurement correction data is data used for correcting image data in measurement processing. The still image file generating unit generates a still image file including the image data corresponding to the image when moving image recording processing is performed. The data writing unit writes the measurement correction data read by the data reading unit in the still image file. The moving image file generating unit generates a moving image file including the image data corresponding to the image when the moving image recording processing is performed. The file recording unit causes the still image file in which the measurement correction data is written, and the moving image file to be associated with each other and to be recorded in a second memory.

According to a second aspect of the present invention, in the first aspect, the file recording unit may record the still image file in the second memory before the moving image file is generated.

According to a third aspect of the present invention, in the first aspect, when a state change from a first state to a second state occurs, the still image file generating unit may generate the still image file. The first state may be a state in which the optical adapter is not mounted at the tip of the endoscope insertion portion. The second state may be a state in which the optical adapter is mounted at the tip of the endoscope insertion portion.

According to a fourth aspect of the present invention, in the first aspect, the file recording unit may apply a first filename to the still image file and may apply a second filename to the moving image file such that the first filename of the still image file in which the measurement correction data is written and the second filename of the moving image file include the same character or the same character string.

According to a fifth aspect of the present invention, in the first aspect, the file recording unit may apply the same filename to the still image file in which the measurement correction data is written and the moving image file.

According to a sixth aspect of the present invention, in the third aspect, the endoscope device may further include a counter that measures a time during which the optical adapter is mounted at the tip of the endoscope insertion portion. When the state change occurs a plurality of times, the file recording unit may apply a filename to a plurality of still image files generated on the basis of the plurality of times of state change. The filename may include the time during which the optical adapter corresponding to each still image file included in the plurality of still image files is mounted at the tip of the endoscope insertion portion.

According to a seventh aspect of the present invention, in the first aspect, the endoscope device may further include a buffer and a file deleting unit. The buffer may temporarily store the image data corresponding to the image and the still image file generated by the still image file generating unit. The file deleting unit may delete the still image file stored in the buffer. In a case in which a remaining capacity of the buffer is smaller than a capacity required to store the image data when the image data corresponding to the image is to be stored in the buffer, at least part of the image data stored in the buffer may be deleted. When at least part of the image data stored in the buffer is deleted, the file deleting unit may delete the still image file corresponding to the deleted image data from the buffer. The file recording unit may record the still image file stored in the buffer in the second memory.

According to an eighth aspect of the present invention, in the first aspect, the endoscope device may further include a measurement unit that performs measurement processing on the basis of the measurement correction data which is written in the still image file recorded in the second memory, and the image data which is included in the moving image file recorded in the second memory.

According to a ninth aspect of the present invention, a file recording method includes a first step, a second step, a third step, a fourth step, a fifth step, a sixth step, a seventh step, and an eighth step. In the first step, an adapter type determining unit determines a type of an optical adapter for measurement mounted at a tip of an endoscope insertion portion. In the second step, a data reading unit reads measurement correction data corresponding to the type of the optical adapter from a first memory. The measurement correction data is data used for correcting image data in measurement processing. In the third step, a still image file generating unit generates a still image file including the image data corresponding to an image of a subject when moving image recording processing is performed. In the fourth step, a data writing unit writes the measurement correction data in the still image file. In the fifth step, a moving image file generating unit generates a moving image file including the image data corresponding to the image when the moving image recording processing is performed. In the sixth step, a file recording unit causes the still image file in which the measurement correction data is written, and the moving image file to be associated with each other and to be recorded in a second memory.

According to a tenth aspect of the present invention, in the ninth aspect, the file recording unit may record the still image file in the second memory before the moving image file is generated.

According to an eleventh aspect of the present invention, in the ninth aspect, when a state change from a first state to a second state occurs, the still image file generating unit may generate the still image file. The first state may be a state in which the optical adapter is not mounted at the tip of the endoscope insertion portion. The second state may be a state in which the optical adapter is mounted at the tip of the endoscope insertion portion.

According to a twelfth aspect of the present invention, in the ninth aspect, the file recording unit may apply a first filename to the still image file and may apply a second filename to the moving image file such that the first filename of the still image file in which the measurement correction data is written and the second filename of the moving image file include the same character or the same character string.

According to a thirteenth aspect of the present invention, in the ninth aspect, the file recording unit may apply the same filename to the still image file in which the measurement correction data is written and the moving image file.

According to a fourteenth aspect of the present invention, in the eleventh aspect, the file recording method may further include a seventh step in which a counter measures a time during which the optical adapter is mounted at the tip of the endoscope insertion portion. When the state change occurs a plurality of times, the file recording unit may apply a filename to a plurality of still image files generated on the basis of the plurality of times of state change. The filename may include the time during which the optical adapter corresponding to each still image file included in the plurality of still image files is mounted at the tip of the endoscope insertion portion.

According a fifteenth aspect of to the present invention, in the ninth aspect, the file recording method may further include an eighth step and a ninth step. In the eighth step, a buffer may temporarily store the image data corresponding to the image and the still image file generated by the still image file generating unit. In the ninth step, the file deleting unit may delete the still image file stored in the buffer. In a case in which a remaining capacity of the buffer is smaller than a capacity required to store the image data when the image data corresponding to the image is to be stored in the buffer, at least part of the image data stored in the buffer may be deleted. When at least part of the image data stored in the buffer is deleted, the file deleting unit may delete the still image file corresponding to the deleted image data from the buffer. The file recording unit may record the still image file stored in the buffer in the second memory.

According to a sixteenth aspect of the present invention, in the ninth aspect, the file recording method may further include a tenth step. In the tenth step, a measurement unit may perform measurement processing on the basis of the measurement correction data which is written in the still image file recorded in the second memory, and the image data which is included in the moving image file recorded in the second memory.

BRIEF DESCRIPTION OF THE DRAWINGS

FIG. 5 is a reference diagram showing a data form of the moving image file in the first embodiment of the present invention.

FIG. 6 is a reference diagram showing a data form of a still image file in the first embodiment of the present invention.

DETAILED DESCRIPTION OF THE INVENTION

Hereinafter, embodiments of the present invention will be described with reference to the drawings.

First Embodiment

Figure 1:
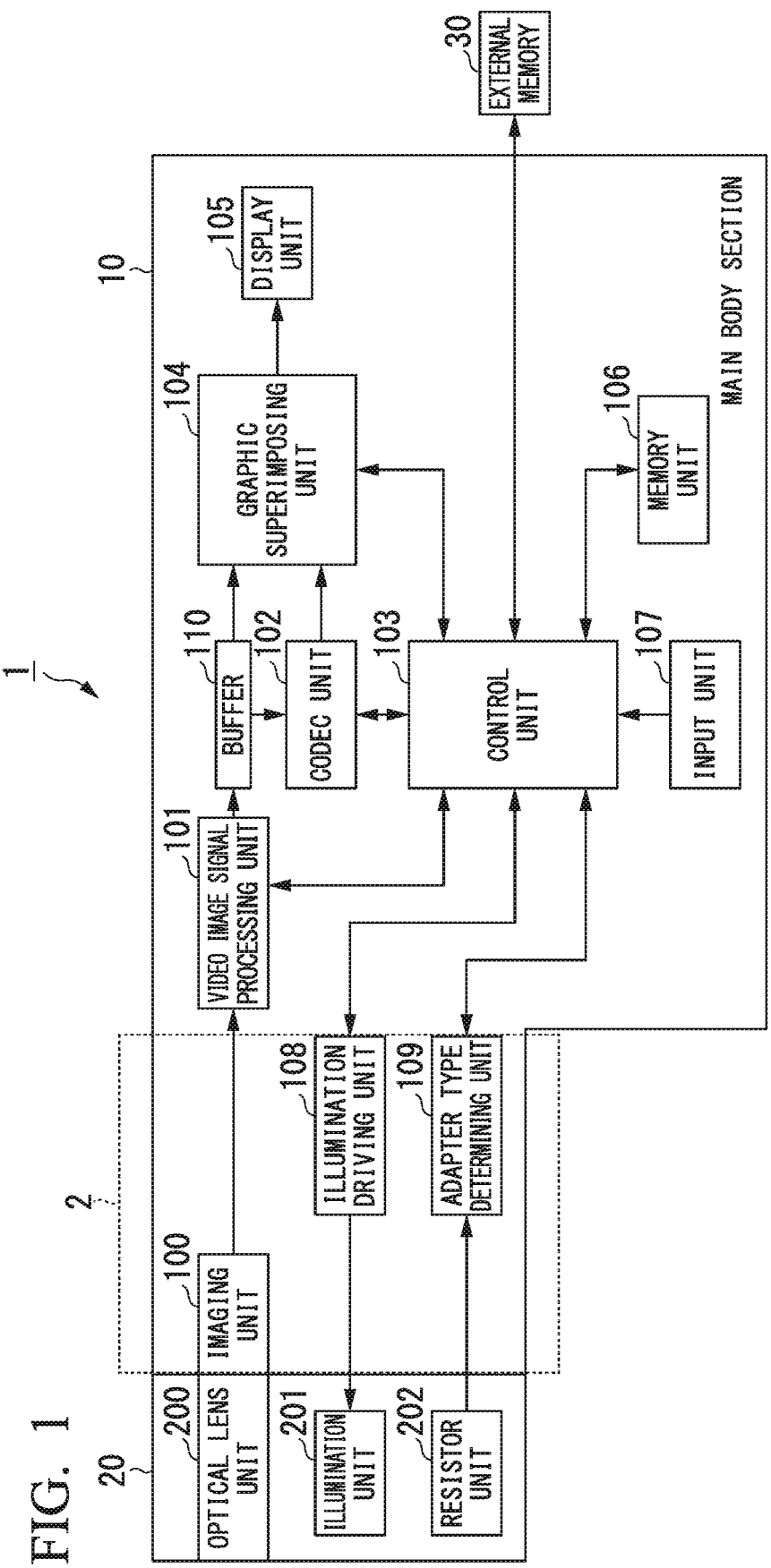
FIG. 1 is a block diagram showing a configuration of an endoscope device according to a first embodiment of the present invention.

FIG. 1 shows a configuration of an endoscope device 1 according to a first embodiment of the present invention. As shown in FIG. 1, the endoscope device 1 includes a main body section 10 that has an endoscope insertion portion 2 inserted into a test object, and an optical adapter 20. The optical adapter 20 can be mounted at a tip of the endoscope insertion portion 2, and the optical adapter 20 can be detached from the tip of the endoscope insertion portion 2.

The main body section 10 has an imaging unit 100, a video image signal processing unit 101, a codec unit 102, a control unit 103, a graphic superimposing unit 104, a display unit 105, a memory unit 106, an input unit 107, an illumination driving unit 108, an adapter type determining unit 109, and a buffer 110. The optical adapter 20 has an optical lens unit 200, an illumination unit 201, and a resistor unit 202.

Light from a subject (measurement target subject) is incident on the optical lens unit 200. Light incident on the optical lens unit 200 is formed into an image by the optical lens unit 200 as a subject image. This subject image is incident on the imaging unit 100. The imaging unit 100 includes an imaging element (image sensor) such as a CCD. The imaging unit 100 captures a subject image and generates a video image signal. Accordingly, the imaging unit 100 generates an image of a subject. The imaging unit 100 is controlled on the basis of the unit of frames. However, the imaging unit 100 may be controlled on the basis of the unit of fields. Therefore, in the following description, a frame may be replaced with a field. The video image signal processing unit 101 performs signal processing such as gain adjustment and white balance with respect to a video image signal output from the imaging unit 100.

A video image signal processed by the video image signal processing unit 101 is output to the graphic superimposing unit 104 and the codec unit 102 via the buffer 110 as moving image data. This moving image data is constituted by image data including a plurality of frames (image frames). The codec unit 102 performs codec processing (compression/expansion) such as motion JPEG or MPEG with respect to moving image data. In addition, the codec unit 102 performs codec processing such as JPEG with respect to still image data constituted by image data of one frame in moving image data.

A moving image file and a still image file generated by the endoscope device 1 can be recorded in an external memory 30 connected to the endoscope device 1. In addition, a moving image file and a still image file recorded in the external memory 30 can be reproduced by the endoscope device 1. When a moving image file or a still image file is recorded in the external memory 30, the codec unit 102 compresses the moving image file or the still image file. The moving image file or the still image file which has been compressed is recorded in the external memory 30 by the control unit 103. When a moving image file or a still image file recorded in the external memory 30 is reproduced, the codec unit 102 reproduces a moving image file or a still image file which is generated before being recorded by expanding the moving image file or the still image file read from the external memory 30 by the control unit 103.

The control unit 103 executes various types of processing for controlling each of the units of the main body section 10, by executing a program stored in the memory unit 106. In addition, the control unit 103 performs measurement. When measurement is performed, still image data input to the codec unit 102 from the video image signal processing unit 101 is output to the control unit 103 without being compressed. The control unit 103 performs measurement by using this still image data. In addition, the control unit 103 can also perform measurement by using moving image data recorded in the external memory 30. The control unit 103 reads image data of one arbitrary frame constituting moving image data recorded in the external memory 30 and performs measurement by using the read image data.

The graphic superimposing unit 104 superimposes graphic data generated by the control unit 103 on image data constituting moving image data or still image data based on the video image signal processed by the video image signal processing unit 101. Alternatively, the graphic superimposing unit 104 superimposes graphic data generated by the control unit 103 on image data constituting moving image data or still image data reproduced by the codec unit 102. Accordingly, the graphic superimposing unit 104 generates a display signal for displaying an image. A menu, a cursor, measurement results, and the like can be displayed together with an endoscopic image by superimposing graphic data on image data constituting an endoscopic image. The display unit 105 displays a moving image or a still image on the basis of the display signal processed by the graphic superimposing unit 104.

The memory unit 106 has a ROM and a RAM. The ROM stores a program for controlling an operation of the control unit 103. The RAM temporarily stores data and the like used for processing performed by the control unit 103. The input unit 107 has an operation unit operated by a user. The input unit 107 outputs a signal based on the operation result of the operation unit to the control unit 103. The control unit 103 identifies an instruction from a user on the basis of the signal output from the input unit 107 and executes various types of processing in accordance with this instruction.

The illumination driving unit 108 drives the illumination unit 201 in response to an instruction from the control unit 103. The illumination unit 201 irradiates a subject with illumination light. The adapter type determining unit 109 determines the type of the optical adapter 20 for measurement mounted at the tip of the endoscope insertion portion 2. Specifically, the adapter type determining unit 109 detects the resistance value of the resistor unit 202 provided in the optical adapter 20 and determines the type of the optical adapter 20 corresponding to the resistance value. The adapter type determining unit 109 outputs optical adapter type data indicating the type of the optical adapter to the control unit 103.

Figure 2:
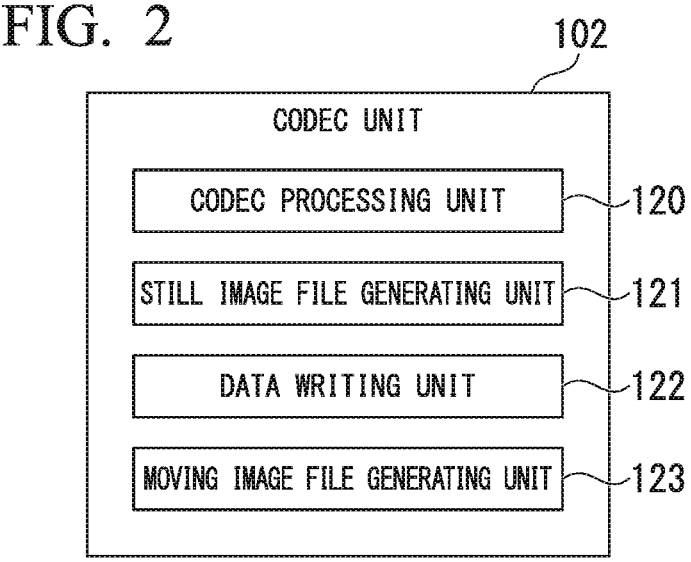
FIG. 2 is a block diagram showing a configuration of a codec unit according to the first embodiment of the present invention.
Figure 3:
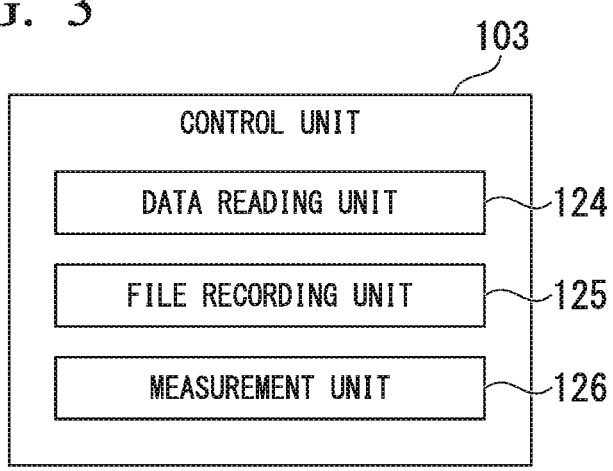
FIG. 3 is a block diagram showing a configuration of a control unit according to the first embodiment of the present invention.

FIG. 2 shows a configuration of the codec unit 102. FIG. 3 shows a configuration of the control unit 103. As shown in FIG. 2, the codec unit 102 has a codec processing unit 120, a still image file generating unit 121, a data writing unit 122, and a moving image file generating unit 123. As shown in FIG. 3, the control unit 103 has a data reading unit 124, a file recording unit 125, and a measurement unit 126.

The codec processing unit 120 performs codec processing. Codec processing includes compression processing for image data (still image data or moving image data) corresponding to an image generated by the imaging unit 100. In addition, codec processing includes expansion processing for image data (still image data) included in a still image file and image data (moving image data) included in a moving image file.

The data reading unit 124 reads measurement correction data corresponding to the type of the optical adapter 20 determined by the adapter type determining unit 109, from the memory unit 106 (first memory). When moving image recording processing is performed, the still image file generating unit 121 generates a still image file including image data (still image data) corresponding to an image generated by the imaging unit 100. The data writing unit 122 writes measurement correction data read by the data reading unit 124 in a still image file generated by the still image file generating unit 121. When the moving image recording processing is performed, the moving image file generating unit 123 generates a moving image file including image data (moving image data) corresponding to an image generated by the imaging unit 100. The file recording unit 125 causes a still image file in which measurement correction data is written by the data writing unit 122, and a moving image file generated by the moving image file generating unit 123 to be associated with each other and to be recorded in the external memory 30 (second memory). The measurement unit 126 performs measurement processing on the basis of the measurement correction data written in a still image file recorded in the external memory 30, and the image data included in a moving image file recorded in the external memory 30.

Each of the units shown in FIGS. 2 and 3 may be constituted by at least one of a processor and a logic circuit. For example, a processor is at least one of a CPU, a digital signal processor (DSP), and a graphic processing unit (GPU). For example, a logic circuit is at least one of an application specific integrated circuit (ASIC) and a field-programmable gate array (FPGA). Each of the units shown in FIGS. 2 and 3 can include one or a plurality of processors. Each of the units shown in FIGS. 2 and 3 can include one or a plurality of logic circuits.

A program executed by a processor may be recorded in a computer readable recording medium. A program includes commands for stipulating an operation of a processor. That is, the function of a processor may be realized by software. For example, a program may be provided through a "computer readable recording medium" such as a flash memory. A program may be transmitted to the endoscope device 1 via a transmission medium or through transmission waves in a transmission medium from a computer saving the program. A "transmission medium" transmitting a program is a medium having a function of transmitting information. A medium having a function of transmitting information includes a network such as the internet (communication network), and a communication channel such as a telephone line (communication line). The program described above may realize part of the foregoing functions. Moreover, the program described above may be a differential file (differential program). A combination of a program, which is already recorded in a computer, and a differential program may realize the foregoing functions.

Measurement correction data is data used for correcting optical distortion for an individual of the optical adapter 20 generated in image data during measurement processing. For example, when the optical adapter 20 has two optical systems, measurement correction data is information such as an expression for correcting geometric distortion of the two optical systems and a focal distance of two lens systems. When a user preliminarily carries out calibration work, measurement correction data is generated on the basis of the result computed by the measurement unit 126. Measurement correction data corresponding to the type of the optical adapter 20 is stored in the memory unit 106 in advance. Measurement correction data is data of a file form which the data writing unit 122 can handle. That is, the file form of measurement correction data has only to be a form in which the data writing unit 122 can read the measurement correction data and the measurement correction data can be written in a still image file.

In the first embodiment, the first memory in which measurement correction data is recorded in advance, and the second memory in which a still image file and a moving image file are recorded differ from each other. The first memory and the second memory may be the same memory. For example, measurement correction data may be recorded in the external memory 30 in advance, and a still image file and a moving image file may be recorded in the external memory 30.

Figure 4:
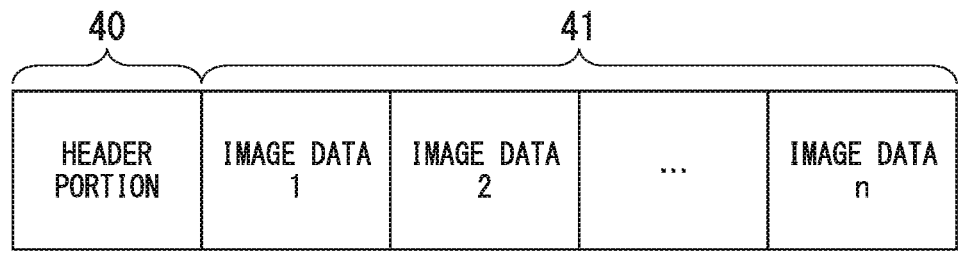
FIG. 4 is a reference diagram showing a data form of a moving image file in the first embodiment of the present invention.

A data form of a moving image file and a still image file in the first embodiment will be described. FIGS. 4 and 5 show a data form of a moving image file. In a first example shown in FIG. 4, a moving image file is constituted by a header portion 40 and a data portion 41. The data portion 41 is constituted by image data in the unit of frames. In FIG. 4, image data of n frames constitutes the data portion 41. The factor n is an integer of 2 or greater. The header portion 40 is constituted by control data and the like corresponding to each frame in image data constituting the data portion 41.

In a second example shown in FIG. 5, moving image data is constituted by unit data 42 in the unit of frames. The unit data 42 is constituted by various kinds of data and image data in the unit of frames. Various kinds of data include control data and the like.

The file form of a still image file is the same as the file form of a still image file generated when an endoscope device in the related art captures a still image. For example, a still image file is a JPEG file. FIG. 6 shows a file structure of a still image file. A still image file is recorded in a form of an exchangeable image file format (EXIF) which is one of formats of a JPEG file. As shown in FIG. 6, a TIFF Header, a 0th image file directory (IFD), an Exif IFD, a 1st IFD, and a Makernote are included within a segment referred to as APP1. A Makernote region, or a User Comment Data region in an Exif IFD is allocated as a storage region of measurement correction data. The data writing unit 122 writes measurement correction data in at least one of these regions. Image data (still image data) is stored in a region for compressed data. Measurement correction data is written in a region different from the region in which the image data is stored in the still image file.

Figure 7:
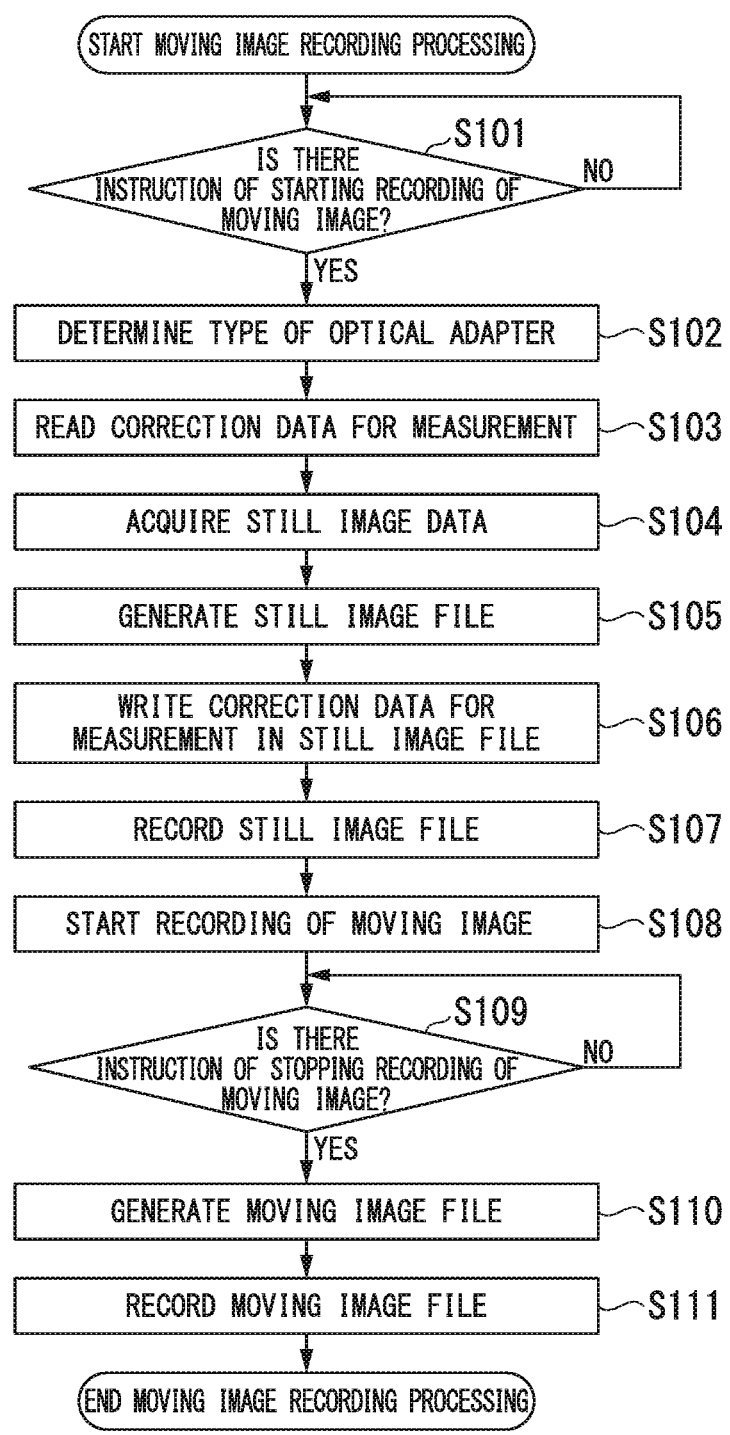
FIG. 7 is a flowchart showing a procedure of moving image recording processing in the first embodiment of the present invention.

Moving image recording processing of the first embodiment will be described. FIG. 7 shows a procedure of moving image recording processing. At the time at which the processing shown in FIG. 7 starts, the imaging unit 100 continuously performs imaging, and the display unit 105 displays a live video image of a subject.

First, the control unit 103 determines whether or not a user has instructed that recording of a moving image be started, on the basis of the signal output from the input unit 107 (Step S101). In Step S101, when a user has not instructed that recording of a moving image be started, determination in Step S101 is repeated.

In Step S101, when a user has instructed that a moving image be recorded, the adapter type determining unit 109 determines the type of the optical adapter 20 mounted at the tip of the endoscope insertion portion 2, and optical adapter type data indicating the type of the mounted optical adapter is output to the control unit 103 (Step S102). After Step S102, the data reading unit 124 reads measurement correction data corresponding to the optical adapter 20 indicated by the optical adapter type data from the memory unit 106. The data reading unit 124 outputs the read measurement correction data to the codec unit 102 (Step S103).

In the moving image recording processing shown in FIG. 7, a timing of determining the type of the optical adapter 20 is a timing immediately after an instruction of starting recording of a moving image is issued. The timing of determining the type of the optical adapter 20 may be a timing at which the optical adapter 20 is mounted at the tip of the endoscope insertion portion 2.

After Step S103, the imaging unit 100 performs imaging of one frame. That is, the imaging unit 100 captures a still image. A video image signal, that is, image data of one frame processed by the video image signal processing unit 101 is stored in the buffer 110. The codec processing unit 120 acquires the image data from the buffer 110 and performs codec processing, that is, compression with respect to the image data (Step S104).

After Step S104, the still image file generating unit 121 generates a still image file including image data, that is, still image data subjected to codec processing (Step S105). After Step S105, the data writing unit 122 writes measurement correction data acquired in Step S103 in the still image file generated in Step S105. The data writing unit 122 outputs the still image file in which the measurement correction data is written to the control unit 103 (Step S106). In this case, the measurement correction data is written in a Makernote region or a User Comment Data region within the still image file.

After Step S106, the file recording unit 125 records the still image file in which the measurement correction data is written in the external memory 30 (Step S107). In this case, the file recording unit 125 applies a predetermined filename to the still image file. For example, the filename of the still image file becomes "0001.jpg". FIG. 6 shows the file structure of the still image file recorded in Step S107.

After Step S107, the control unit 103 starts recording of a moving image (Step S108). In this case, the imaging unit 100 continuously performs imaging. That is, the imaging unit 100 captures a moving image. A video image signal of each frame processed by the video image signal processing unit 101 is sequentially stored in the buffer 110. Recording of a moving image continues until an instruction of stopping recording of a moving image is issued.

After Step S108, the control unit 103 determines whether or not a user has instructed that recording of a moving image be stopped, on the basis of the signal output from the input unit 107 (Step S109). In Step S109, when a user has not instructed that recording of a moving image be stopped, determination in Step S109 is repeated.

In Step S109, when a user has instructed that recording of a moving image be stopped, the control unit 103 stops recording of a moving image. Accordingly, the imaging unit 100 stops performing imaging. The codec processing unit 120 acquires the image data stored in the buffer 110 from the buffer 110 and performs codec processing, that is, compression with respect to the image data. The moving image file generating unit 123 generates a moving image file including image data, that is, moving image data subjected to codec processing. That is, the moving image file generating unit 123 generates a moving image file including the image data stored in the buffer 110 at the time at which an instruction of stopping recording of a moving image is issued. The moving image file generating unit 123 outputs the generated moving image file to the control unit 103 (Step S110).

After Step S110, the file recording unit 125 records the moving image file in the external memory 30 (Step S111).

The file recording unit 125 applies the same filename to the still image file in which the measurement correction data is written, and the moving image file. For example, the filename of the moving image file becomes "0001.avi". That is, in the still image file and the moving image file, the filename excluding the filename extension becomes the same as each other. In this manner, both a still image file and a moving image file corresponding thereto can be associated with each other by applying the same filename "0001" thereto.

The file recording unit 125 may apply a first filename to a still image file and may apply a second filename to a moving image file such that the first filename of the still image file in which the measurement correction data is written and the second filename of the moving image file include the same character or the same character string. Both a still image file and a moving image file can be associated with each other by causing the filenames thereof to include the same character or the same character string.

In the processing shown in FIG. 7, the still image file generating unit 121 generates a still image file before a moving image file is generated by the moving image file generating unit 123. In addition, the file recording unit 125 records the still image file in the external memory 30 before the moving image file is generated by the moving image file generating unit 123. Specifically, the processing from Step S102 to Step S107 is performed before recording of a moving image is started (Step S108). The still image file may be generated and recorded after the moving image file is recorded. Alternatively, the still image file may be generated and recorded after recording of a moving image is started (Step S108) and before the moving image file is recorded.

Figure 8:
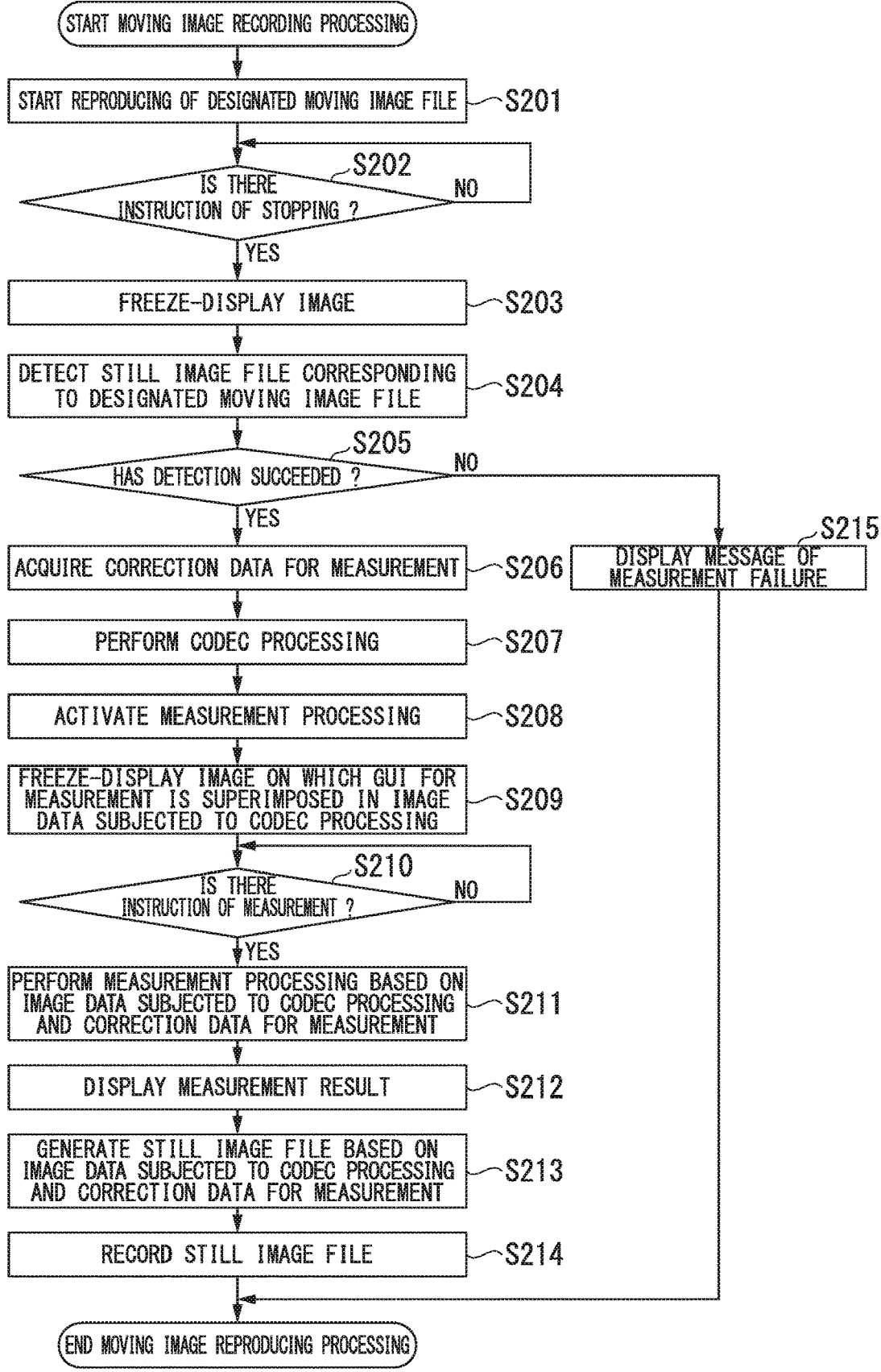
FIG. 8 is a flowchart showing a procedure of moving image reproducing processing in the first embodiment of the present invention.

Moving image reproducing processing of the first embodiment will be described. FIG. 8 shows a procedure of moving image reproducing processing. Moving image reproducing processing includes measurement processing.

When a user has instructed that a moving image file be reproduced, via the input unit 107, the control unit 103 reads the moving image file designated by the user from the external memory 30 and starts reproduction of the moving image file (Step S201). After reproduction of the moving image file is started, the control unit 103 sequentially outputs image data of each frame included in the moving image file to the codec unit 102. The codec processing unit 120 performs codec processing, that is, expansion with respect to the image data sequentially output from the control unit 103. The display unit 105 sequentially displays images on the basis of the image data subjected to codec processing. That is, the display unit 105 displays a moving image.

A user searches for an image intended for measurement while watching the moving image displayed by the display unit 105. When the image intended for measurement is found, the user instructs that reproducing be temporarily stopped, via the input unit 107. Accordingly, the user can designate image data of a measurement target. The control unit 103 determines whether or not a user has instructed that reproduction of the moving image be temporarily stopped, on the basis of the signal output from the input unit 107 (Step S202). In Step S202, when a user has not instructed that reproduction of the moving image be temporarily stopped, the display unit 105 continues to display the moving image.

In Step S202, when a user has instructed that reproduction of the moving image be temporarily stopped, the control unit 103 stops reproduction of the moving image and causes the display unit 105 to freeze-display an image based on the image data of the frame subjected to an instruction of temporarily stopping (Step S203).

After Step S203, the control unit 103 performs detection processing of the still image file to which the same filename is applied as the filename of the moving image file including the image data corresponding to the image which is currently freeze-displayed. That is, the control unit 103 searches for a still image file to which the same filename is applied as the filename of the moving image file in the external memory 30 (Step S204). After Step S204, the control unit 103 determines whether or not detection of the still image file has succeeded in Step S204 (Step S205).

In Step S205, when detection of the still image file has failed, the control unit 103 outputs graphic data for displaying a message which informs a user of the fact that measurement cannot be performed to the graphic superimposing unit 104. The graphic superimposing unit 104 superimposes the graphic data output from the control unit 103 on the image data corresponding to the freeze-displayed image. Accordingly, the graphic superimposing unit 104 generates a display signal. The display unit 105 freeze-displays the image on which the message described above is superimposed, on the basis of the display signal (Step S215).

In Step S205, when detection of the still image file has succeeded, the control unit 103 reads the still image file from the external memory 30. The control unit 103 outputs the read still image file to the codec unit 102. The codec unit 102 acquires measurement correction data from a Makernote region or a User Comment Data region within the still image file. The codec unit 102 outputs the acquired measurement correction data to the control unit 103 (Step S206).

After Step S206, the control unit 103 reads image data of one frame corresponding to the freeze-displayed image from the external memory 30 and outputs the image data to the codec unit 102. The codec processing unit 120 performs codec processing, that is, expansion with respect to the image data output from the control unit 103. The codec processing unit 120 outputs the expanded image data to the graphic superimposing unit 104 (Step S207).

After Step S207, the control unit 103 activates measurement processing (Step S208). After Step S208, the control unit 103 outputs graphic data for displaying a GUI for measurement processing to the graphic superimposing unit 104. The graphic superimposing unit 104 superimposes the graphic data output from the control unit 103 on the image data output from the codec unit 102. Accordingly, the graphic superimposing unit 104 generates a display signal. The display unit 105 freeze-displays an image on which the GUI for measurement processing is superimposed, on the basis of the display signal (Step S209).

After Step S209, the control unit 103 determines whether or not a user has instructed that measurement be performed, on the basis of the signal output from the input unit 107 (Step S210). For example, a user can instruct that measurement be performed by designating the type of a measurement method or designating a measurement point. In Step S210, when a user has not instructed that measurement be performed, determination in Step S210 is repeated.

In Step S210, when a user has instructed that measurement be performed, the control unit 103 acquires the image data subjected to codec processing in Step S207 from the codec unit 102. The measurement unit 126 performs measurement processing as instructed by a user, on the basis of the image data subjected to codec processing in Step S207 and the measurement correction data acquired in Step S206. Accordingly, the measurement unit 126 calculates three-dimensional coordinates of the measurement point in a subject and calculates the dimensions of the subject (Step S211).

After Step S211, the control unit 103 outputs graphic data for displaying measurement results to the graphic superimposing unit 104. The graphic superimposing unit 104 superimposes the graphic data output from the control unit 103 on the image data output from the codec unit 102. Accordingly, the graphic superimposing unit 104 generates a display signal. The display unit 105 freeze-displays an image on which measurement results are superimposed, on the basis of the display signal (Step S212).

After Step S212, the codec processing unit 120 performs codec processing, that is, compression for a still image with respect to the image data expanded in Step S207. The still image file generating unit 121 generates a still image file including image data, that is, still image data subjected to codec processing. The data writing unit 122 writes the measurement correction data acquired in the still image file generated in Step S206. The data writing unit 122 outputs the still image file in which the measurement correction data is written to the control unit 103 (Step S213). After Step S213, the file recording unit 125 records the still image file in which the measurement correction data is written in the external memory 30 (Step S214).

The processing in Step S213 may be performed even when an instruction of measurement is not issued in Step S210. For example, there are cases in which a user does not desire to perform measurement processing during this moving image reproducing processing but desires to carry out measurement processing in the future on the basis of the image data at the time at which reproduction of the moving image is temporarily stopped. In this case, measurement processing can be quickly performed by using the still image file recorded in Step S213.

In the processing shown in FIG. 8, after measurement processing, a still image file in which the measurement correction data is written is generated. Measurement results may be applied to the still image data generated after measurement processing, instead of the measurement correction data.

The endoscope device according to each of the aspects of the present invention need not have a configuration other than the configuration corresponding to each of the endoscope insertion portion 2, the adapter type determining unit 109, the imaging unit 100, the data reading unit 124, the still image file generating unit 121, the data writing unit 122, the moving image file generating unit 123, and the file recording unit 125.

As described above, measurement correction data is written in a still image file. A device which can handle a still image file can use measurement correction data written in the still image file. Therefore, it is possible to avoid an increase in data capacity of the moving image data itself, and it is possible to avoid an increase in the number of kinds of files to be handled by the device in order to perform measurement processing.

The codec unit 102 which can handle a still image file can write measurement correction data in the still image file and can acquire the measurement correction data written in the still image file. Therefore, it is possible to avoid an increase in the number of kinds of files to be handled by the codec unit 102.

The measurement unit 126 performs measurement processing on the basis of the measurement correction data written in the still image file, and the image data included in the moving image file. Therefore, measurement can be performed by using moving image data.

The memory capacity for recording a still image file can be ensured by recording a still image file before a moving image file is generated by the moving image file generating unit 123.

Second Embodiment

A second embodiment of the present invention will be described by using the endoscope device 1 of the first embodiment. In the second embodiment, when a state change from a first state to a second state occurs, the still image file generating unit 121 generates a still image file. The first state is a state in which the optical adapter 20 is not mounted at the tip of the endoscope insertion portion 2. The second state is a state in which the optical adapter 20 is mounted at the tip of the endoscope insertion portion 2.

In the first embodiment, a still image is captured on the basis of an instruction of recording a moving image from a user, and a still image file is generated. In contrast, in the second embodiment, when the optical adapter 20 is exchanged during recording of a moving image, recording of a moving image continues, and a still image is captured and a still image file is generated during recording of a moving image. Therefore, in a case in which the optical adapter 20 is exchanged once during recording of a moving image, when recording of a moving image is started, and when the optical adapter 20 is exchanged, a still image file is generated. That is, when the optical adapter 20 is exchanged once during recording of a moving image, two still image files are generated.

Figure 9:
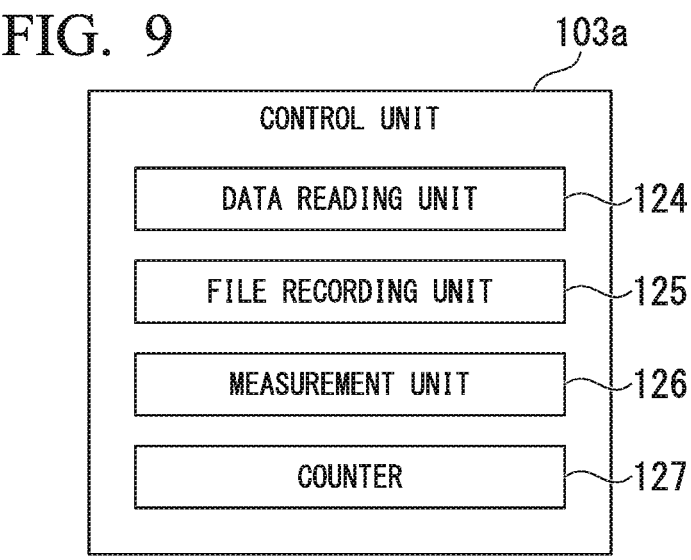
FIG. 9 is a block diagram showing a configuration of a control unit according to a second embodiment of the present invention.

In the endoscope device 1 of the second embodiment, the control unit 103 is replaced with a control unit 103a shown in FIG. 9. FIG. 9 shows a configuration of the control unit 103a. Regarding the configuration shown in FIG. 9, points different from the configuration shown in FIG. 3 will be described.

The control unit 103a has a counter 127 in addition to the configuration of the control unit 103 shown in FIG. 3. The counter 127 measures the filming time of a moving image. In addition, the counter 127 measures the time during which the optical adapter 20 is mounted at the tip of the endoscope insertion portion 2. That is, the counter 127 measures the time from the timing at which the optical adapter 20 is mounted at the tip of the endoscope insertion portion 2 to the timing at which the optical adapter 20 is detached from the tip of the endoscope insertion portion 2. In other words, the counter 127 measures the time during which the state of the optical adapter 20 mounted at the tip of the endoscope insertion portion 2 continues. When a state change has occurred a plurality of times, the file recording unit 125 applies a filename including the time, during which the optical adapter 20 corresponding to each still image file included in a plurality of still image files is mounted at the tip of the endoscope insertion portion 2, to the plurality of still image files generated on the basis of a plurality of times of state changes.

Regarding the points other than those described above, the configuration shown in FIG. 9 is the same as the configuration shown in FIG. 3.

Figure 10:
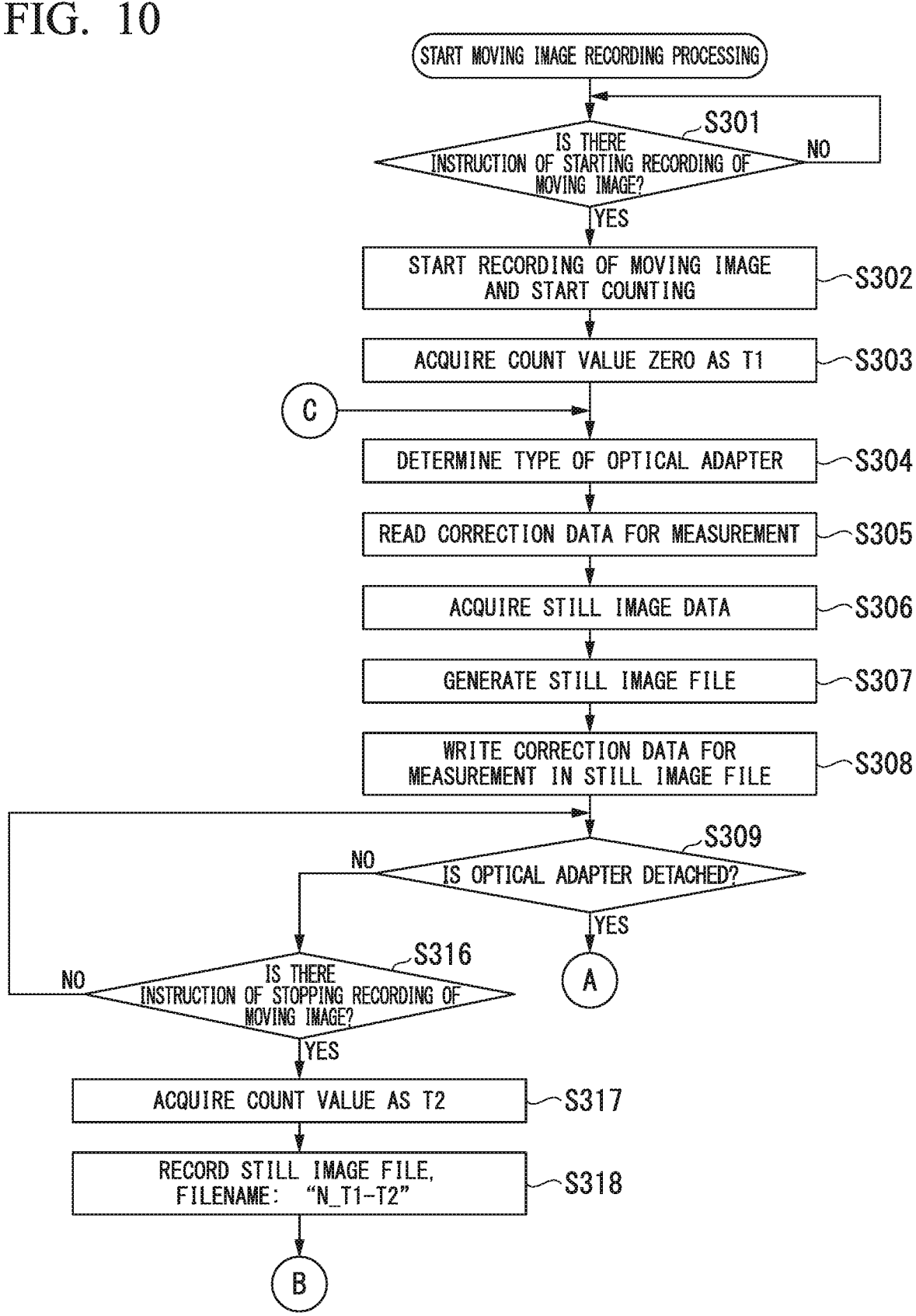
FIG. 10 is a flowchart showing a procedure of moving image recording processing in the second embodiment of the present invention.
Figure 11:
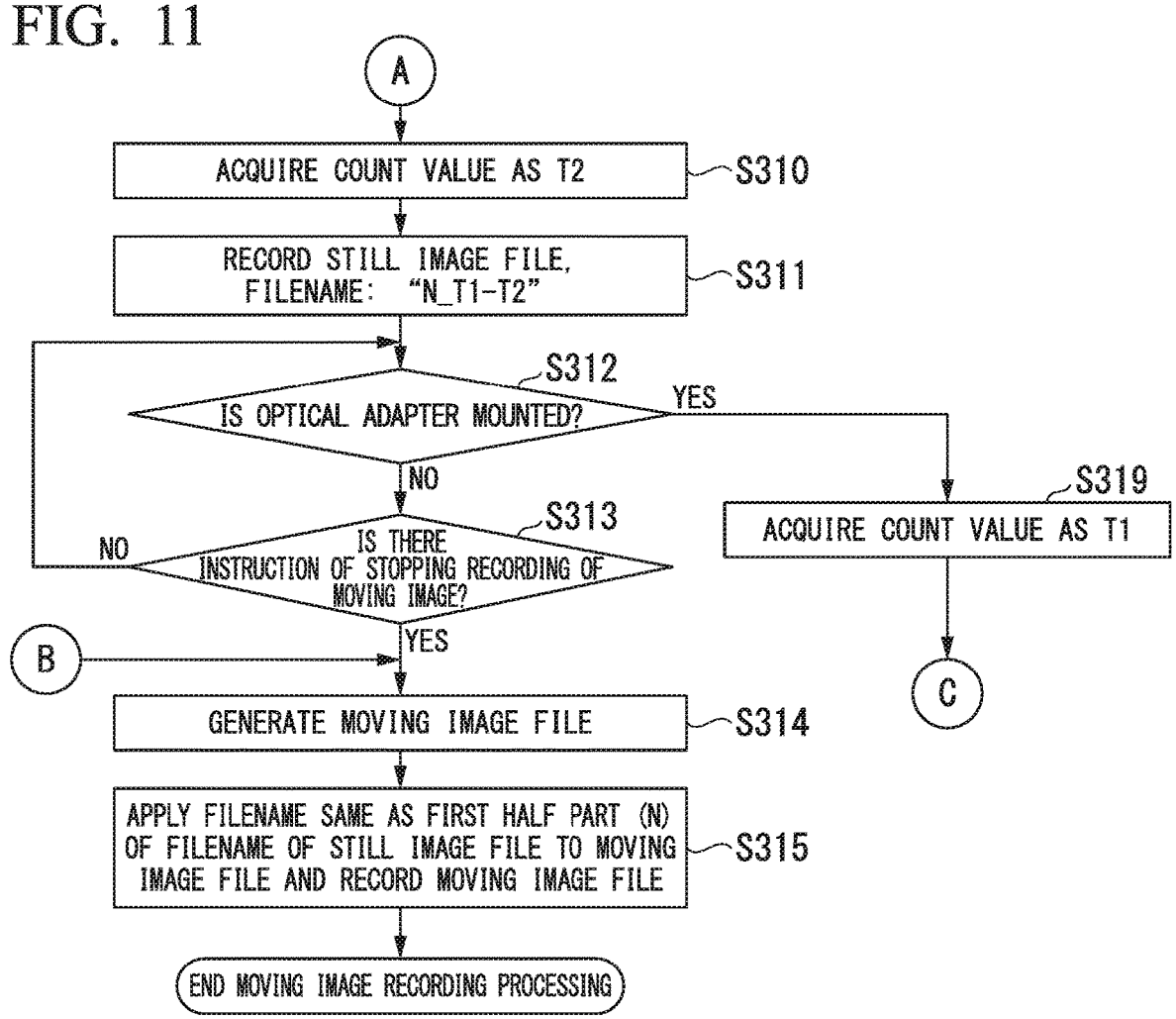
FIG. 11 is a flowchart showing another procedure of moving image recording processing in the second embodiment of the present invention.

Moving image recording processing of the second embodiment will be described. FIGS. 10 and 11 show procedures of moving image recording processing. Description of the same processing as the moving image recording processing shown in FIG. 7 will be omitted.

Processing in Step S301 is the same as the processing in Step S101 in FIG. 7. In Step S301, when a user has instructed that recording of a moving image be started, the control unit 103a starts recording of a moving image, and the counter 127 starts counting (measurement) (Step S302). In this case, the imaging unit 100 continuously performs imaging. That is, the imaging unit 100 captures a moving image. A video image signal, that is, image data of each frame processed by the video image signal processing unit 101 is sequentially stored in the buffer 110. Recording of a moving image continues until an instruction of stopping recording of a moving image is issued. The count value of the counter 127 sequentially increases from an initial value. The initial value of the count value is zero.

After Step S302, the control unit 103a acquires the initial value of the count value of the counter 127, that is, zero as a time T1 (Step S303). After Step S303, the processing from Step S304 to Step S308 is performed. Each of the processing from Step S304 to Step S308 is the same as each of the processing from Step S102 to Step S106 shown in FIG. 7.

After Step S308, the control unit 103a determines whether or not the optical adapter 20 is detached from the tip of the endoscope insertion portion 2 (Step S309). In Step S309, when the optical adapter 20 is detached from the tip of the endoscope insertion portion 2, the control unit 103a acquires the count value of the counter 127 as a time T2 (Step S310).

After Step S310, the file recording unit 125 records the still image file in which the measurement correction data is written in the external memory 30. That is, when a state change from the first state to the second state occurs, the file recording unit 125 records a still image file in the external memory 30 (Step S311). The first state is a state in which the optical adapter 20 is not mounted at the tip of the endoscope insertion portion 2. The second state is a state in which the optical adapter 20 is mounted at the tip of the endoscope insertion portion 2. In this case, the file recording unit 125 applies a predetermined filename to the still image file. For example, the filename of the still image file becomes "N_T1-T2.jpg". The factor N included in the filename is an arbitrary number. A user may designate N. Alternatively, the control unit 103a may automatically determine N. The factor T1 included in the filename is the time T1 acquired by the control unit 103a. The factor T2 included in the filename is the time T2 acquired by the control unit 103a. That is, the filename of a still image file includes information indicating the period during which the optical adapter 20 is mounted at the tip of the endoscope insertion portion 2. The filename of a firstly recorded still image file includes the timing at which moving image recording processing is started and the timing at which the optical adapter 20 is detached from the tip of the endoscope insertion portion 2. For example, when the optical adapter 20 is detached from the tip of the endoscope insertion portion 2 at the timing after 100 seconds has elapsed, the filename of the firstly recorded still image file becomes "N_0-100.jpg".

After Step S311, the control unit 103a determines whether or not the optical adapter 20 is mounted at the tip of the endoscope insertion portion 2 (Step S312). In Step S312, when the optical adapter 20 is mounted at the tip of the endoscope insertion portion 2, the control unit 103a acquires the count value of the counter 127 as the time T1 (Step S319). After Step S319, the processing in Step S304 is performed. When the processing in Step S311 is performed after the processing in Step S319 is performed, the filename of the still image file includes the timing at which the optical adapter 20 is mounted at the tip of the endoscope insertion portion 2, and the timing at which the optical adapter 20 is detached from the tip of the endoscope insertion portion 2.

In Step S312, when the optical adapter 20 is not mounted at the tip of the endoscope insertion portion 2, the control unit 103a determines whether or not a user has instructed that recording of a moving image be stopped, on the basis of the signal output from the input unit 107 (Step S313). In Step S313, when a user has not instructed that recording of a moving image be stopped, the processing in Step S312 is performed.

In Step S313, when a user has instructed that recording of a moving image be stopped, the control unit 103a stops recording of a moving image. Accordingly, the imaging unit 100 stops performing imaging. The codec processing unit 120 acquires the image data stored in the buffer 110 from the buffer 110 and performs codec processing, that is, compression with respect to the image data. The moving image file generating unit 123 generates a moving image file including image data, that is, moving image data subjected to codec processing. That is, the moving image file generating unit 123 generates a moving image file including the image data stored in the buffer 110 at the time at which an instruction of stopping recording of a moving image is issued. The moving image file generating unit 123 outputs the generated moving image file to the control unit 103a (Step S314).

After Step S314, the file recording unit 125 records the moving image file in the external memory 30 (Step S315). In this case, the file recording unit 125 applies the first half part of the filename of the still image file, that is, the same filename as N to the moving image file. For example, the filename of the moving image file becomes "N.avi". That is, in the still image file and the moving image file, at least part of the filename excluding the filename extension becomes the same as each other.

In Step S309, when the optical adapter 20 is not detached from the tip of the endoscope insertion portion 2, the control unit 103a determines whether or not a user has instructed that recording of a moving image be stopped, on the basis of the signal output from the input unit 107 (Step S316). In Step S316, when a user has not instructed that recording of a moving image be stopped, the processing in Step S309 is performed.

In Step S316, when a user has instructed that recording of a moving image be stopped, the control unit 103a acquires the count value of the counter 127 as the time T2 (Step S317). After Step S317, the file recording unit 125 records the still image file in which the measurement correction data is written in the external memory 30 (Step S318). In this case, the file recording unit 125 applies a predetermined filename to the still image file. For example, the filename of the still image file becomes "N_T1-T2.jpg". This filename is similar to the filename applied to the still image file in Step S311. After Step S318, the processing in Step S314 is performed.

After the optical adapter 20 is detached from the tip of the endoscope insertion portion 2, even when the same optical adapter 20 is remounted at the tip of the endoscope insertion portion 2, a still image file is generated and recorded by the processing described above.

Figure 12:
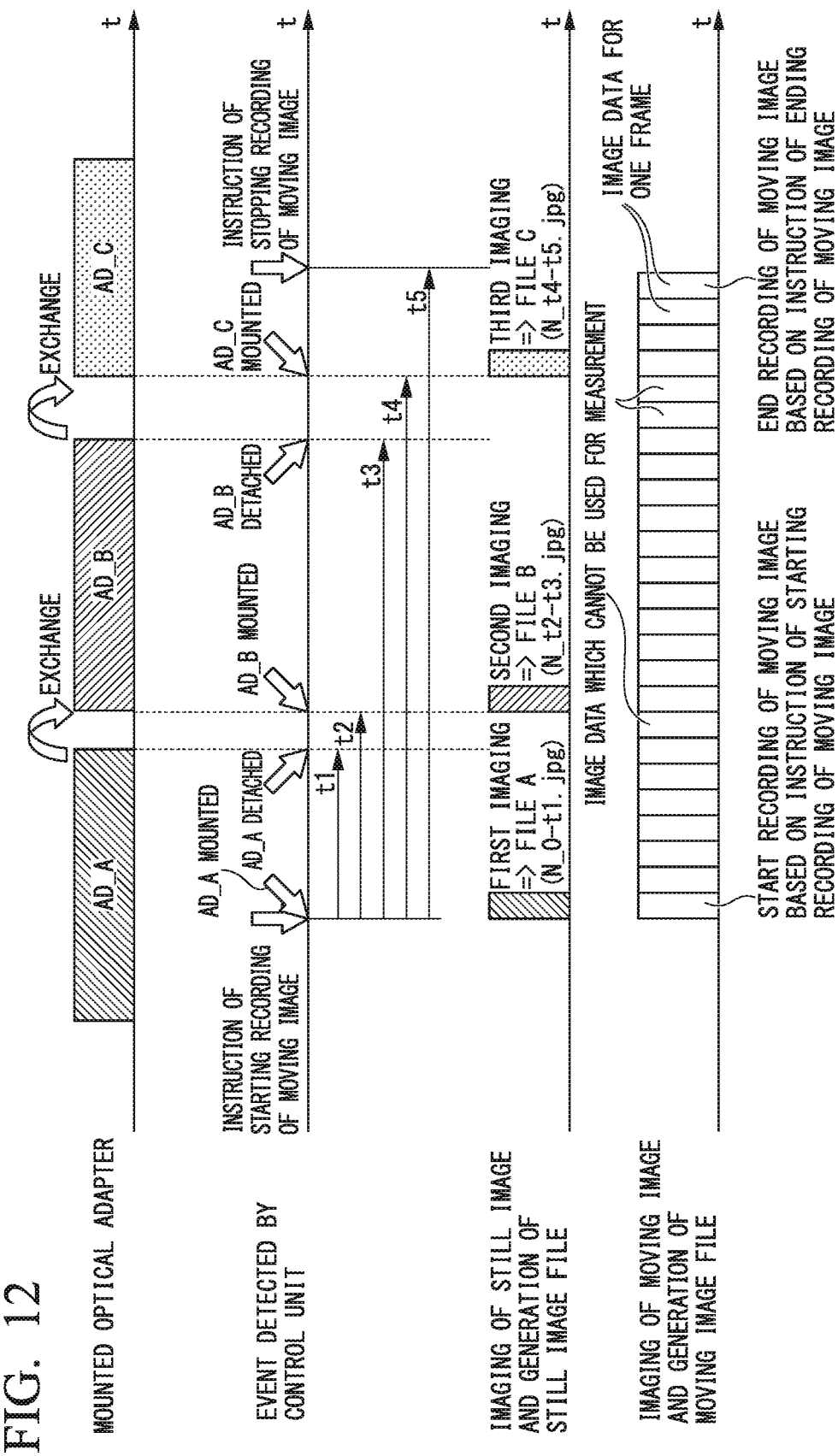
FIG. 12 is a timing chart showing a situation of generating a still image file and a moving image file when a plurality of optical adapters are sequentially mounted at a tip of an endoscope insertion portion in the second embodiment of the present invention.

FIG. 12 shows a situation of generating a still image file and a moving image file when a plurality of optical adapters 20 are sequentially mounted at the tip of the endoscope insertion portion 2. The horizontal axis in FIG. 12 indicates the time.

First, an optical adapter AD_A is mounted at the tip of the endoscope insertion portion 2. Thereafter, when a user instructs that recording of a moving image be started, the imaging unit 100 continuously performs imaging. Image data of each frame is stored in the buffer 110. The image data of a first frame is acquired as still image data (Step S306), and a still image file A is generated (Step S307). When a time t1 has elapsed after the timing at which an instruction of starting recording of a moving image is issued, the optical adapter AD_A is detached from the tip of the endoscope insertion portion 2. In this case, the still image file A is recorded in the external memory 30 (Step S311). The filename of the still image file A becomes "N_0-t1.jpg".

When a time t2 has elapsed after the timing at which an instruction of starting recording of a moving image is issued, an optical adapter AD_B is mounted at the tip of the endoscope insertion portion 2. In this case, still image data is acquired (Step S306), and a still image file B is generated (Step S307). When a time t3 has elapsed after the timing at which an instruction of starting recording of a moving image is issued, the optical adapter AD_B is detached from the tip of the endoscope insertion portion 2. In this case, the still image file B is recorded in the external memory 30 (Step S311). The filename of the still image file B becomes "N_t2-t3.jpg".

When a time t4 has elapsed after the timing at which an instruction of starting recording of a moving image is issued, an optical adapter AD_C is mounted at the tip of the endoscope insertion portion 2. In this case, still image data is acquired (Step S306), and a still image file C is generated (Step S307). When a time t5 has elapsed after the timing at which an instruction of starting recording of a moving image is issued, a user instructs that recording of a moving image be stopped. In this case, the still image file C is recorded in the external memory 30 (Step S318). The filename of the still image file C becomes "N_t4-t5.jpg". Moreover, a moving image file including the image data stored in the buffer 110 is generated (Step S314), and the moving image file is recorded in the external memory 30 (Step S315).

Figure 13:
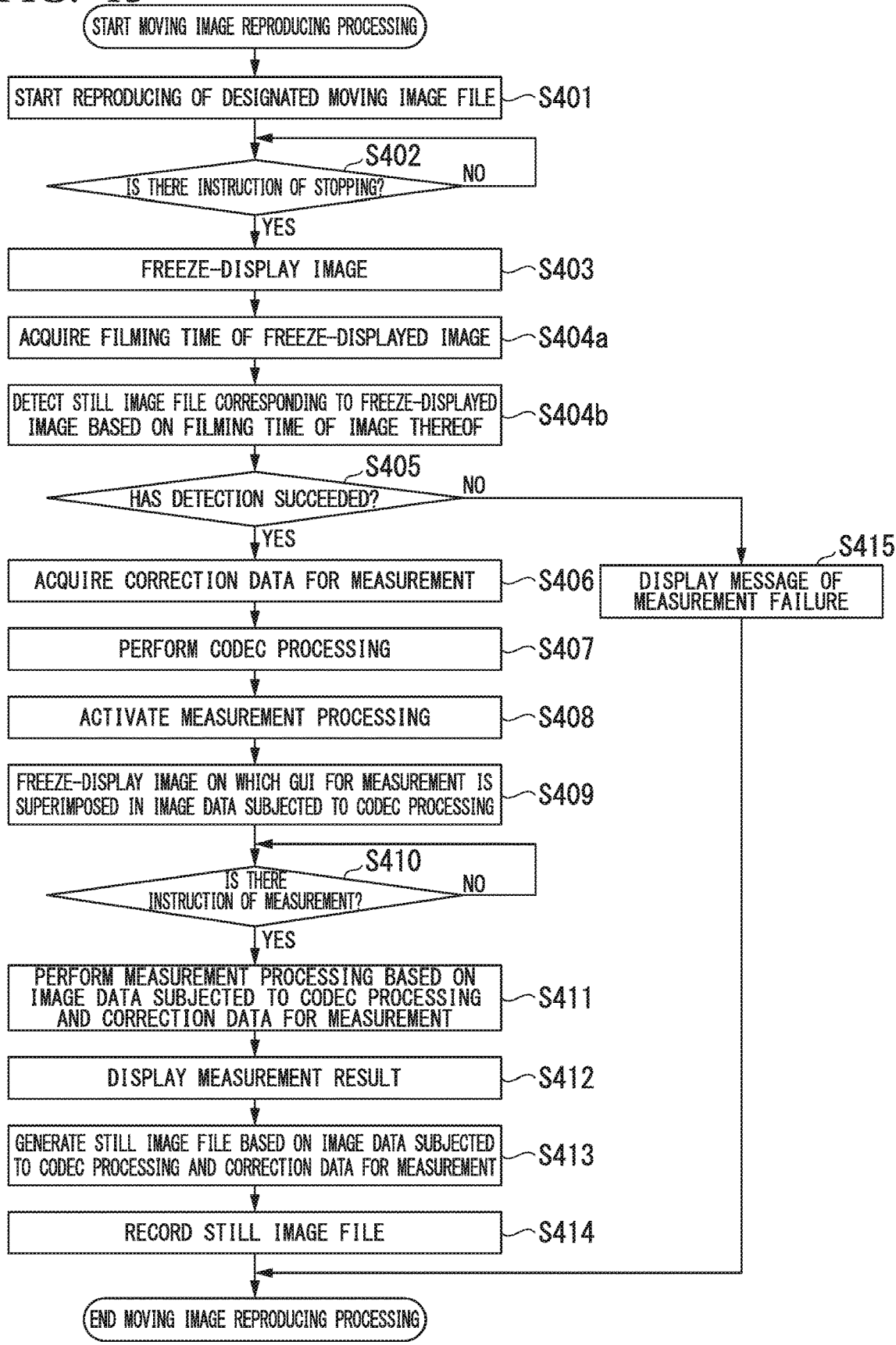
FIG. 13 is a flowchart showing a procedure of moving image reproducing processing in the second embodiment of the present invention.

Moving image reproducing processing of the second embodiment will be described. FIG. 13 shows a procedure of moving image reproducing processing. Description of the same processing as the moving image reproducing processing shown in FIG. 8 will be omitted.

Each of the processing from Step S401 to Step S403 is the same as each of the processing from Step S201 to Step S203 in FIG. 8. After Step S403, the control unit 103a acquires the filming time of image data corresponding to the image which is currently freeze-displayed (Step S404a). For example, the filming time is applied to each piece of image data constituting a moving image file. The filming time may be calculated on the basis of the frame number of image data. The filming time is a time having the timing at which recording of a moving image is started as a reference. After Step S404a, the control unit 103a performs detection processing of a still image file corresponding to the image which is currently freeze-displayed, on the basis of the filming time acquired in Step S404a. That is, the control unit 103a searches for a still image file corresponding to the image data, in image data constituting the moving image file, designated by a user (Step S404b).

After Step S404b, the processing in Step S405 is performed. Each of the processing from Step S405 to Step S415 is the same as each of the processing from Step S205 to Step S215 in FIG. 8.

Image data recorded during a period in which the optical adapter 20 is detached and the optical adapter 20 is not mounted at the tip of the endoscope insertion portion 2 cannot be used in measurement. Therefore, when an image based on the image data recorded during this period is freeze-displayed, the control unit 103a may cause the display unit 105 to display a warning message indicating the fact that measurement cannot be performed.

For example, when the still image file A, the still image file B, and the still image file C described by using FIG. 12 are recorded in the external memory 30, the following processing is performed in Step S404a and Step S404b. In Step S404a, the control unit 103a acquires a filming time to of an image data F1 corresponding to the image which is currently freeze-displayed. For example, the filming time to is larger than the time t2 and is smaller than the time t3 (t2<tf1<t3). In Step S404b, the control unit 103a searches for a still image file in which the time included in the filename includes the filming time tf1.

Figure 14:
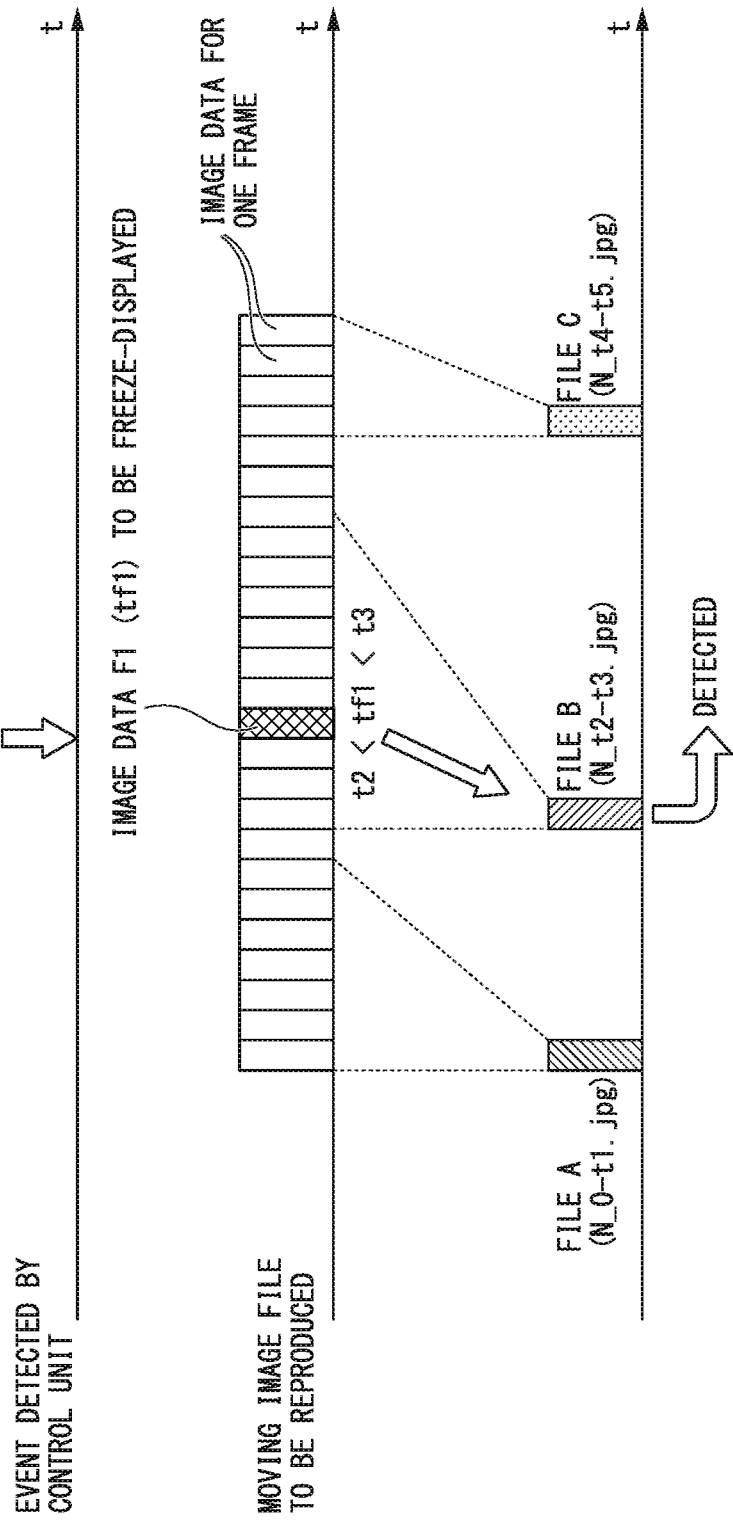
FIG. 14 is a timing chart showing a situation of detecting a still image file corresponding to a freeze-displayed image in the second embodiment of the present invention.

FIG. 14 shows a situation of detecting a still image file corresponding to a freeze-displayed image. The horizontal axis in FIG. 14 indicates the time.

A user instructs that reproduction of a moving image be temporarily stopped while the moving image file is reproduced. In this case, an image based on the image data of which the filming time is tf1 is freeze-displayed. The time included in the filename of the still image file A is 0-t1. The time included in the filename of the still image file B is t2-t3. The time included in the filename of the still image file C is t4-t5. The time t2-t3 of the times included in the filenames of the still image files includes the filming time tf1. Therefore, in Step S404b, the control unit 103a detects the still image file B.

In the second embodiment, measurement correction data is written in a still image file. A device which can handle a still image file can use measurement correction data written in the still image file. Therefore, it is possible to avoid an increase in data capacity of the moving image data itself, and it is possible to avoid an increase in the number of kinds of files to be handled by the device in order to perform measurement processing.

When the optical adapter 20 is exchanged while moving image recording processing is performed, the control unit 103a can acquire a still image file corresponding to the freeze-displayed image, that is, the image of a measurement target. Therefore, the control unit 103a can acquire appropriate measurement correction data corresponding to the image of a measurement target.

Third Embodiment

A third embodiment of the present invention will be described by using the endoscope device 1 of the second embodiment. In the third embodiment, points different from the first and second embodiments will be described.

In the first and second embodiments, recording of a moving image is started in response to an instruction from a user. In the third embodiment, recording of a moving image is automatically started when the system is activated.

The buffer 110 constitutes a ring buffer. Image data generated in moving image recording processing is stored in the ring buffer. When the data capacity of image data in the ring buffer reaches a predetermined level, old image data is deleted, and then new image data is stored in the ring buffer. That is, image data is overwritten.

When the optical adapter 20 is exchanged, similar to the second embodiment, a still image file including measurement correction data is generated, and the still image file is recorded in association with a moving image file. As described above, old image data of a moving image is deleted. When the image data corresponding to the still image file including measurement correction data is deleted, the still image file including the measurement correction data is also deleted.

Figure 15:
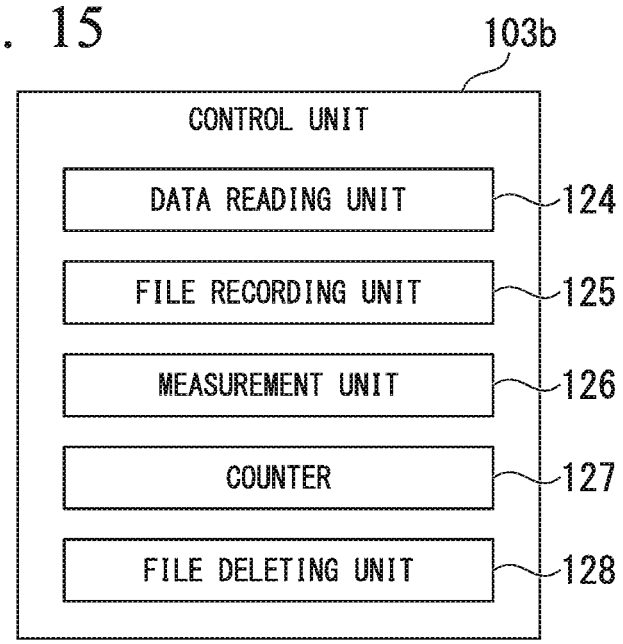
FIG. 15 is a block diagram showing a configuration of a control unit according to a third embodiment of the present invention.

In the endoscope device 1 of the third embodiment, the control unit 103 is replaced with a control unit 103b shown in FIG. 15. FIG. 15 shows a configuration of the control unit 103b. Regarding the configuration shown in FIG. 15, points different from the configuration shown in FIG. 9 will be described.

The control unit 103b has a file deleting unit 128, in addition to the configuration of the control unit 103a shown in FIG. 9. Regarding the configuration other than the file deleting unit 128, the configuration shown in FIG. 15 is similar to the configuration shown in FIG. 9.

The buffer 110 temporarily stores image data corresponding to an image generated by the imaging unit 100, and a still image file generated by the still image file generating unit 121. The file deleting unit 128 deletes a still image file stored in the buffer 110. In a case in which the remaining capacity of the buffer 110 is smaller than the capacity required to store image data when the image data corresponding to an image generated by the imaging unit 100 is to be stored in the buffer 110, at least part of the image data stored in the buffer 110 is deleted. When at least part of the image data stored in the buffer 110 is deleted, the file deleting unit 128 deletes a still image file corresponding to the deleted image data from the buffer 110. The file recording unit 125 records the still image file stored in the buffer 110 in the external memory 30 (second memory).

Figure 16:
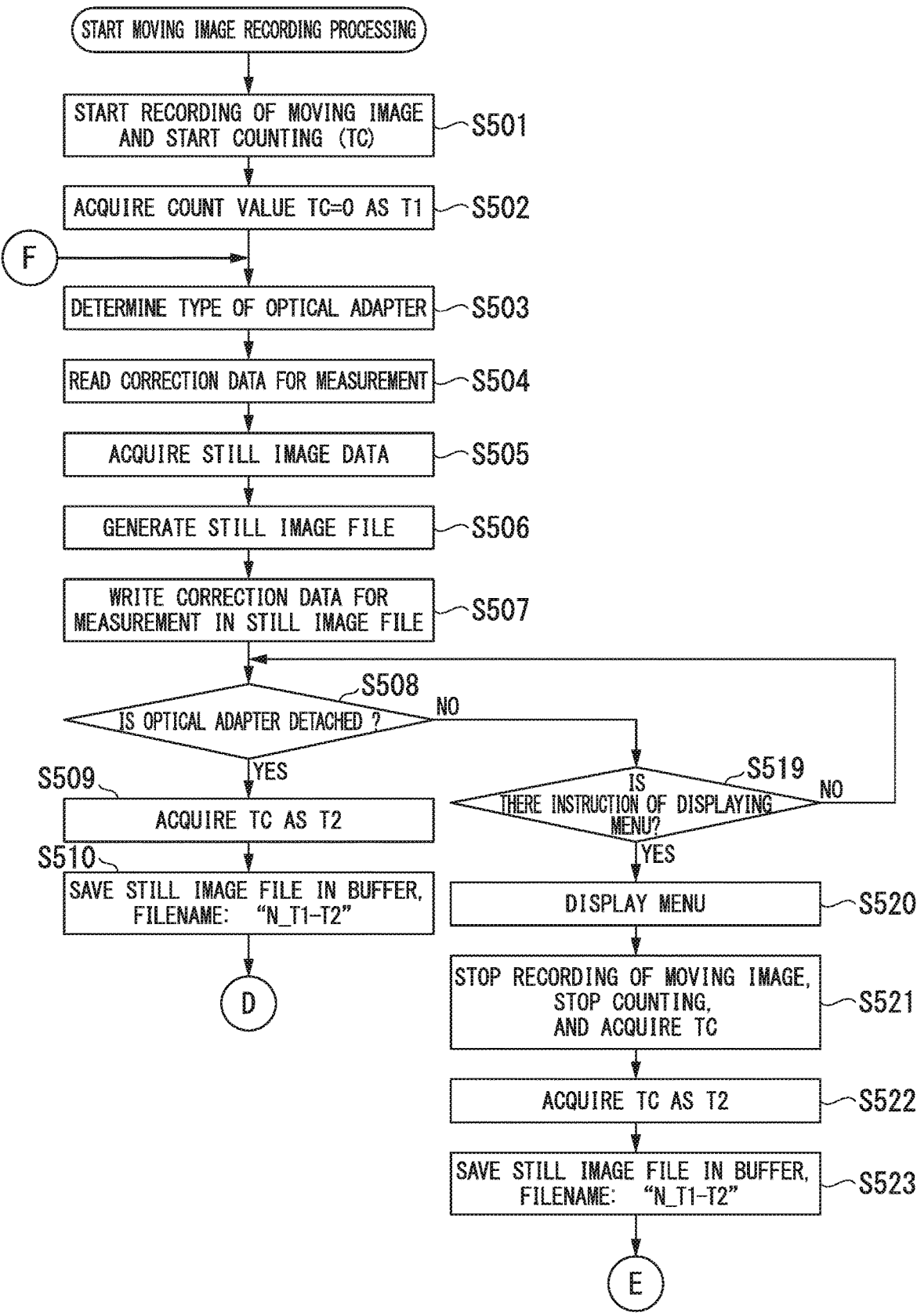
FIG. 16 is a flowchart showing a procedure of moving image recording processing in the third embodiment of the present invention.
Figure 17:
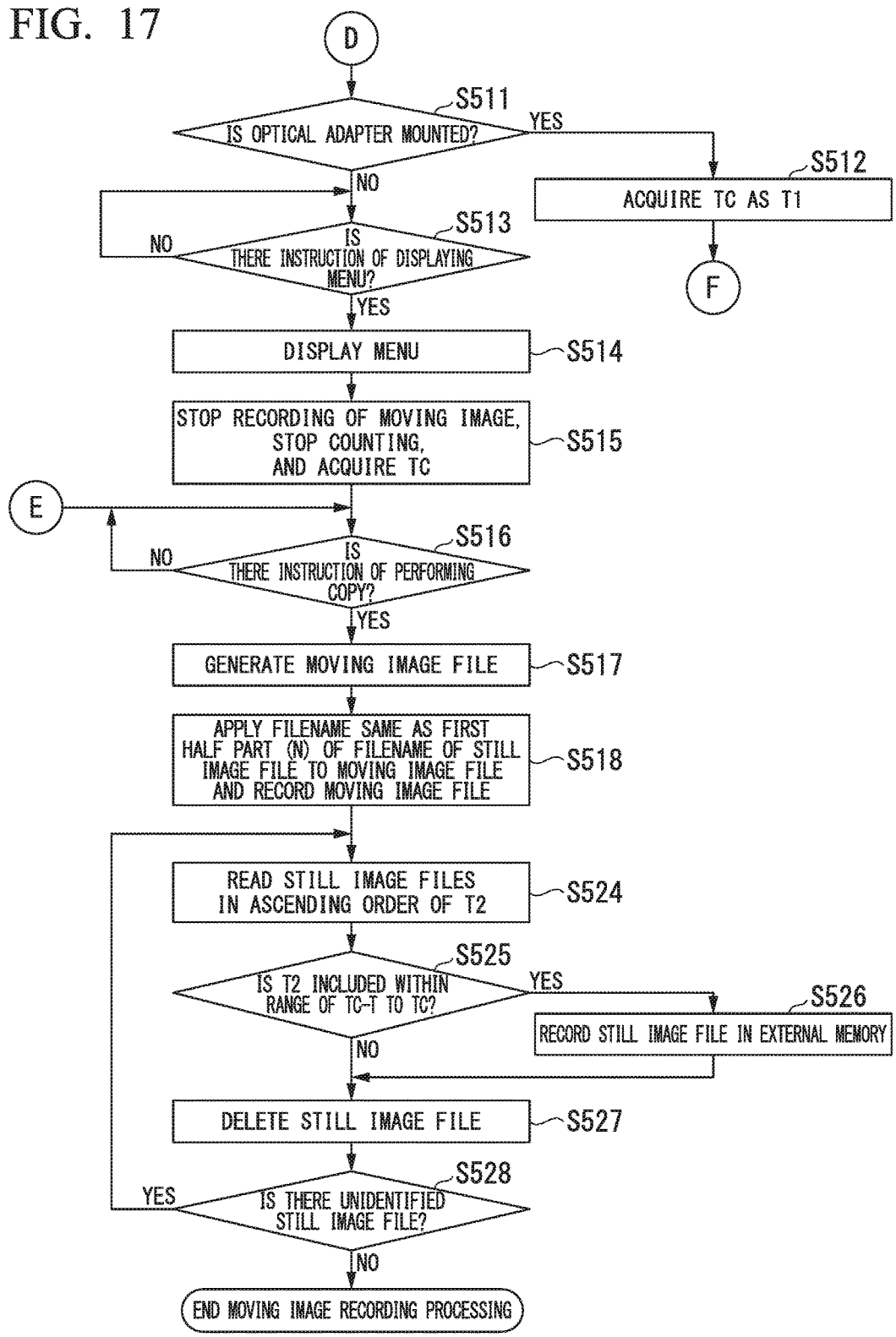
FIG. 17 is a flowchart showing a procedure of moving image recording processing in the third embodiment of the present invention.

Moving image recording processing of the third embodiment will be described. FIGS. 16 and 17 show procedures of moving image recording processing. Description of the same processing as the moving image recording processing shown in FIG. 7 will be omitted.

When power is supplied to the endoscope device 1 and the system is activated, the control unit 103b starts recording of a moving image without depending on an instruction of recording a moving image from a user. Accordingly, the imaging unit 100 continuously performs imaging. That is, the imaging unit 100 captures a moving image. A video image signal, that is, image data of each frame processed by the video image signal processing unit 101 is sequentially stored in the buffer 110. In addition, the control unit 103b causes the counter 127 to start counting (measurement) (Step S501). The buffer 110 is a ring buffer, and a recordable time of the buffer 110 is T. The recordable time T is a recording time of a moving image which can be saved in the buffer 110. Image data generated during the nearest period having the same length as the recordable time T is accumulated in the buffer 110. A count value TC of the counter 127 sequentially increases from an initial value. The initial value of the count value TC is zero.

After Step S501, the control unit 103b acquires the initial value of the count value TC of the counter 127, that is, zero as the time T1 (Step S502). After Step S502, the processing in Step S503 is performed. Each of the processing from Step S503 to Step S507 is the same as each of the processing from Step S102 to Step S106 in FIG. 7.

After Step S507, the control unit 103b determines whether or not the optical adapter 20 is detached from the tip of the endoscope insertion portion 2 (Step S508). In Step S508, when the optical adapter 20 is detached from the tip of the endoscope insertion portion 2, the control unit 103b acquires the count value TC of the counter 127 as the time T2 (Step S509).

After Step S509, the file recording unit 125 saves the still image file in which the measurement correction data is written in the buffer 110 (Step S510). In this case, the file recording unit 125 applies a predetermined filename to the still image file. For example, the filename of the still image file becomes "N_T1-T2.jpg". The factor N included in the filename is an arbitrary number. The factor T1 included in the filename is the time T1 acquired by the control unit 103b. The factor T2 included in the filename is the time T2 acquired by the control unit 103b. That is, the filename of a still image file includes information indicating the period during which the optical adapter 20 is mounted at the tip of the endoscope insertion portion 2.

After Step S510, the control unit 103b determines whether or not the optical adapter 20 is mounted at the tip of the endoscope insertion portion 2 (Step S511). In Step S511, when the optical adapter 20 is mounted at the tip of the endoscope insertion portion 2, the control unit 103b acquires the count value TC of the counter 127 as the time T1 (Step S512). After Step S512, the processing in Step S503 is performed. When the processing in Step S510 is performed after the processing in Step S512 is performed, the filename of the still image file includes the timing at which the optical adapter 20 is mounted at the tip of the endoscope insertion portion 2, and the timing at which the optical adapter 20 is detached from the tip of the endoscope insertion portion 2.

In Step S511, when the optical adapter 20 is not mounted at the tip of the endoscope insertion portion 2, the control unit 103b determines whether or not a user has instructed that a menu be displayed, on the basis of the signal output from the input unit 107 (Step S513). In Step S513, when a user has not instructed that the menu be displayed, determination in Step S513 is repeated.

In Step S513, when a user has instructed that the menu be displayed, the control unit 103b outputs graphic data for displaying the menu to the graphic superimposing unit 104. The graphic superimposing unit 104 superimposes the graphic data output from the control unit 103b on image data read from the buffer 110. Accordingly, the graphic superimposing unit 104 generates a display signal. The display unit 105 displays an image on which the menu is superimposed, on the basis of the display signal (Step S514). The displayed menu includes "COPY" which is a GUI for a user inputting an instruction of recording a moving image file including the image data stored in the buffer 110 from the buffer 110 to the external memory 30.

After Step S514, the control unit 103b stops recording of a moving image and causes the counter 127 to stop counting. Accordingly, the imaging unit 100 stops performing imaging. Moreover, the control unit 103b acquires the count value TC at the time at which the counter 127 has stopped counting (Step S515).

After Step S515, the control unit 103b determines whether or not an instruction of performing COPY is issued, on the basis of the signal output from the input unit 107 (Step S516). In Step S516, when an instruction of performing COPY is not issued, determination in Step S516 is repeated.

In Step S516, when an instruction of performing COPY is issued, the codec processing unit 120 acquires the image data stored in the buffer 110 from the buffer 110 and performs codec processing, that is, compression with respect to the image data. The moving image file generating unit 123 generates a moving image file including image data, that is, moving image data subjected to codec processing. That is, the moving image file generating unit 123 generates a moving image file including the image data stored in the buffer 110 at the time at which an instruction of stopping recording of a moving image is issued. The moving image file generating unit 123 outputs the generated moving image file to the control unit 103b (Step S517).

After Step S517, the file recording unit 125 records the moving image file in the external memory 30 (Step S518). In this case, the file recording unit 125 applies the first half part of the filename of the still image file, that is, the same filename as N to the moving image file. For example, the filename of the moving image file becomes "N.avi". That is, in the still image file and the moving image file, at least part of the filename excluding the filename extension becomes the same as each other.

In Step S508, when the optical adapter 20 is not detached from the tip of the endoscope insertion portion 2, the control unit 103b determines whether or not a user has instructed that the menu be displayed, on the basis of the signal output from the input unit 107 (Step S519). In Step S519, when a user has not instructed that the menu be displayed, the processing in Step S508 is performed.

In Step S519, when a user has instructed that the menu be displayed, the processing in Step S520 is performed. Each of the processing in Step S520 and Step S521 is the same as each of the processing in Step S514 and Step S515. After Step S521, the processing in Step S522 is performed. Each of the processing in Step S522 and Step S523 is the same as each of the processing in Step S509 and Step S510. After Step S523, the processing in Step S516 is performed.

For example, after the optical adapter 20 is exchanged, the count value TC of the counter 127 is acquired as the time T1 in Step S512. Thereafter, in a state in which the optical adapter 20 is not detached from the tip of the endoscope insertion portion 2 in Step S508, a user instructs that the menu be displayed in Step S519. Therefore, the count value TC of the counter 127 is acquired as the time T2 in Step S521. The filename applied to a still image file in Step S523 includes the time T1 and the time T2.

After the moving image file is recorded in the external memory 30 in Step S518, the control unit 103b determines whether or not a plurality of still image files stored in the buffer 110 are to be recorded in the external memory 30. First, the control unit 103b selects a still image file having the smallest T2 included in the filename from the plurality of still image files stored in the buffer 110. The control unit 103b reads the selected still image file from the buffer 110 (Step S524). When Step S524 is performed a plurality of times, the plurality of still image files stored in the buffer 110 are read from the buffer 110 in the ascending order of T2.

After Step S524, the control unit 103b determines whether or not T2 included in the filename of the selected still image file is within a range of (TC-T) to TC (Step S525). The factor TC is a count value acquired in Step S515. In Step S525, when T2 included in the filename of the selected still image file is not included within the range of (TC-T) to TC, the processing in Step S527 is performed.

In Step S525, when T2 included in the filename of the selected still image file is included within the range of (TC-T) to TC, the file recording unit 125 records the selected still image file in the external memory 30 (Step S526). The start time of the recorded moving image file is a time going back in time by the recordable time T of the buffer 110 from the end time TC of recording of a moving image, that is, the time of (TC-T). The end time of the moving image file is an ending time of recording of a moving image, that is, the time of TC. Therefore, when T2 is included within the range of (TC-T) to TC, image data to which measurement correction data in the still image file having T2 included in the filename can be applied is included in the moving image file.

In a case in which it is determined that T2 is included within the range of (TC-T) to TC, the still image file having T2 included in the filename is necessary when measurement is performed on the basis of the image data constituting the moving image file. Therefore, the still image file is recorded in the external memory 30.

After Step S526, the file deleting unit 128 deletes the still image file stored in the buffer 110 (Step S527). When T2 is not included within the range of (TC-T) to TC, that is, when T2 is beyond the range of (TC-T) to TC, the image data corresponding to the still image file having T2 included in the filename is not included in the moving image file. Therefore, the still image file is not recorded in the external memory 30 and is deleted from the buffer 110.

As described above, when the time at which a still image file is generated is not included in the period from the time at which image data of the first frame in the moving image file is generated to the time at which image data of the last frame in the moving image file is generated, the file deleting unit 128 deletes the still image file stored in the buffer 110. The file recording unit 125 applies the filename including the time at which the still image file is generated to the still image file.

After Step S527, the control unit 103b determines whether or not an unidentified still image file is present in the buffer 110 (Step S528). In Step S528, when an unidentified still image file is present in the buffer 110, the processing in Step S524 is performed. In Step S528, when an unidentified still image file is not present in the buffer 110, moving image recording processing ends.

Figure 18:
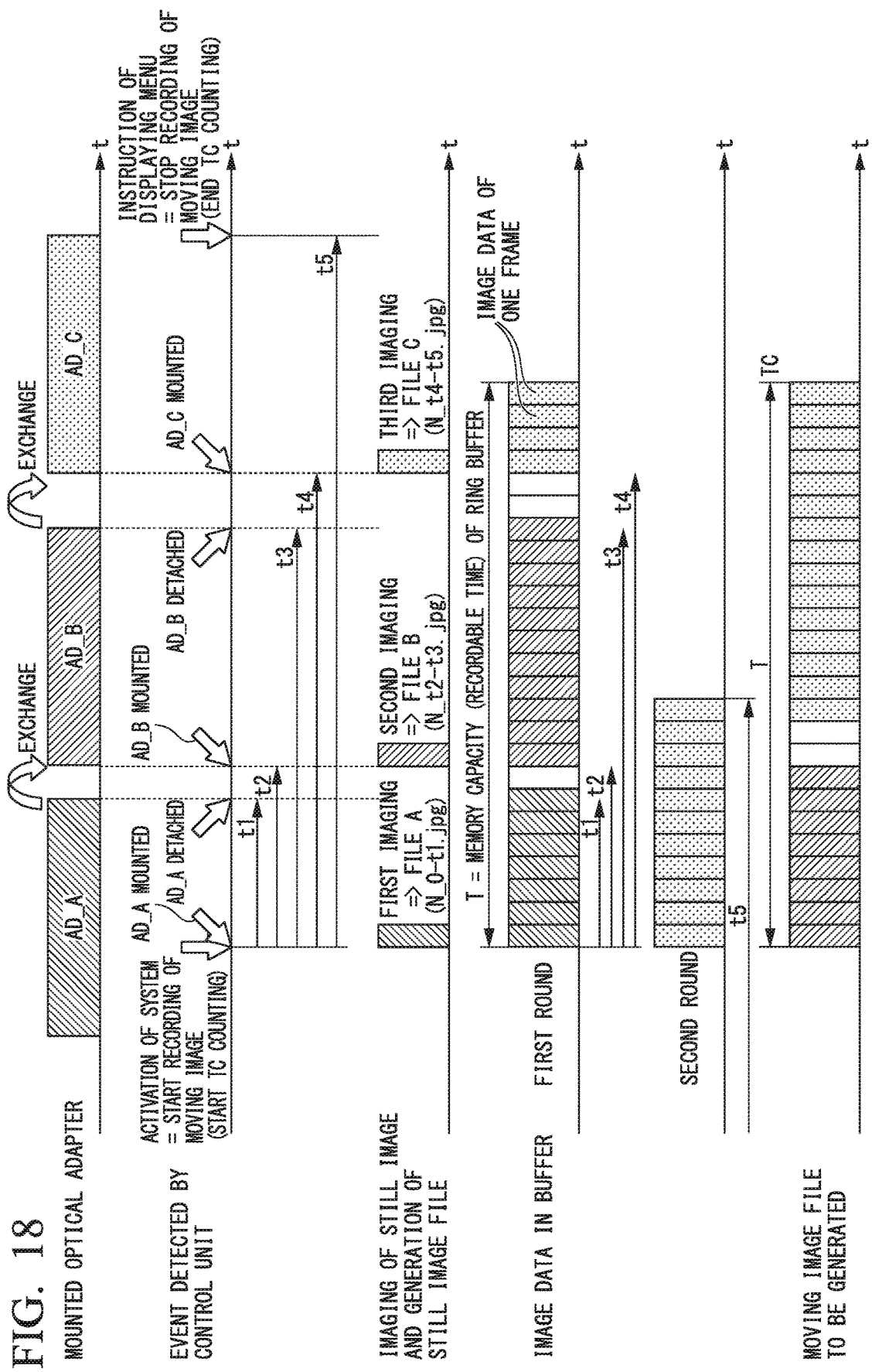
FIG. 18 is a timing chart showing a situation of generating a still image file and a moving image file when a plurality of optical adapters are sequentially mounted at a tip of an endoscope insertion portion in the third embodiment of the present invention.

FIG. 18 shows a situation of generating a still image file and a moving image file when the plurality of optical adapters 20 are sequentially mounted at the tip of the endoscope insertion portion 2. The horizontal axis in FIG. 18 indicates the time.

First, the optical adapter AD_A is mounted at the tip of the endoscope insertion portion 2. Thereafter, when the system of the endoscope device 1 is activated, recording of a moving image is started, and the imaging unit 100 continuously performs imaging. Image data of each frame is stored in the buffer 110. The image data of the first frame is acquired as still image data (Step S505), and the still image file A is generated (Step S506). When the time t1 has elapsed after the timing at which recording of a moving image is started, the optical adapter AD_A is detached from the tip of the endoscope insertion portion 2. In this case, the still image file A is saved in the buffer 110 (Step S510). The filename of the still image file A becomes "N_0-t1.jpg".

When the time t2 has elapsed after the timing at which recording of a moving image is started, the optical adapter AD_B is mounted at the tip of the endoscope insertion portion 2. In this case, still image data is acquired (Step S505), and the still image file B is generated (Step S506). When the time t3 has elapsed after the timing at which recording of a moving image is started, the optical adapter AD_B is detached from the tip of the endoscope insertion portion 2. In this case, the still image file B is saved in the buffer 110 (Step S510). The filename of the still image file B becomes "N_t2-t3.jpg".

When the time t4 has elapsed after the timing at which recording of a moving image is started, the optical adapter AD_C is mounted at the tip of the endoscope insertion portion 2. In this case, still image data is acquired (Step S505), and the still image file C is generated (Step S506). When the time t5 has elapsed after the timing at which recording of a moving image is started, a user instructs that the menu be displayed. In this case, the still image file C is saved in the buffer 110 (Step S523). The filename of the still image file C becomes "N_t4-t5.jpg".

When a user has instructed that COPY be performed, the moving image file including the image data stored in the buffer 110 is generated (Step S517), and the moving image file is recorded in the external memory 30 (Step S518). Thereafter, determination regarding a still image file is performed.

Determination regarding a still image file will be described in detail. In the following description, it is assumed that T=1,000 s, t1=300 s, t2=350 s, t3=750 s, t4=850 s, t5=1,400 s, and TC=1,400 s. In this case, the filename of the still image file A becomes "N_0-300". The filename of the still image file B becomes "N_350-750". The filename of the still image file C becomes "N_850-1400". In addition, (TC-T) which is the start time of the moving image file is 400 s, and TC which is the end time of the moving image file is 1,400 s.

At first, the still image file A is selected (Step S524). The factor "t1=300 s" corresponding to T2 included in the filename of the still image file A is not included within a range of "TC-T=400 s" to "TC=1,400 s" (Step S525). Therefore, the still image file A is not recorded in the external memory 30 and is deleted from the buffer 110 (Step S527).

Next, the still image file B is selected (Step S524). The factor "t3=750 s" corresponding to T2 included in filename of the still image file B is included within the range of "TC-T=400 s" to "TC=1,400 s" (Step S525). Therefore, the still image file B is recorded in the external memory 30 (Step S526) and is deleted from the buffer 110 (Step S527).

It is obvious that the moving image file shown in FIG. 18 includes moving image data (image data group) to which measurement correction data for the optical adapter AD_B is applied. The still image file B is recorded in the external memory 30 for measurement processing in the future.

Next, the still image file C is selected (Step S524). The factor "t5=1,400 s" corresponding to T2 of the filename of the still image file C is included within the range of "TC-T=400 s" to "TC=1,400 s" (Step S525). Therefore, the still image file C is recorded in the external memory 30 (Step S526) and is deleted from the buffer 110 (Step S527).

In the third embodiment, measurement correction data is written in a still image file. A device which can handle a still image file can use measurement correction data written in the still image file. Therefore, it is possible to avoid an increase in data capacity of the moving image data itself, and it is possible to avoid an increase in the number of kinds of files to be handled by the device in order to perform measurement processing.

In the third embodiment, image data constituting the moving image data is saved in the buffer 110, and the image data in the buffer 110 is deleted (overwritten) in order from the older data. There are cases in which after a still image file including measurement correction data is generated, image data constituting moving image data corresponding to the still image file is deleted from (overwritten in) the buffer 110. In this case, it is obvious that the still image file is not used in measurement. Therefore, a still image file which is not used in measurement is deleted from the buffer 110 without being recorded in the external memory 30. Accordingly, the capacity of the external memory 30 can be reduced. In addition, a load of recording data in the external memory 30 is lightened.

Modification Example of Third Embodiment

Figure 19:
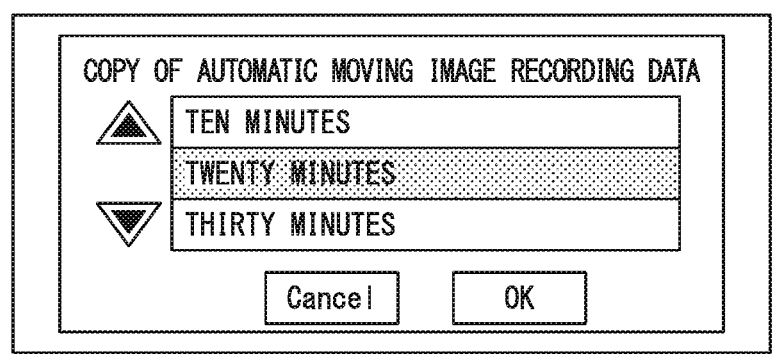
FIG. 19 is a reference diagram showing a GUI in a modification example of the third embodiment of the present invention.

In the third embodiment, when a moving image file is recorded in the external memory 30, all the image data in the buffer 110 is copied. The size of the image data to be copied may be able to be designated by a user. FIG. 19 shows an example of a GUI for a user selecting the copying time of a moving image. For example, as the times for image data to be copied, three choices of 10 minutes, 20 minutes, and 30 minutes are prepared. A user can select an arbitrary time from the three times. For example, when 20 minutes is selected, a moving image file including the image data, in the image data in the buffer 110, generated during the nearest period of 20 minutes is copied to the external memory 30.

The time which can be selected by a user is not limited to the time exemplified in FIG. 19. The kind of time which can be selected by a user may be two kinds. Alternatively, the kind of time which can be selected by a user may be more than three kinds.

Modification Examples of First to Third Embodiments

Moving image reproducing processing may be performed in an external device different from the endoscope device 1. For example, the external device is a personal computer. The external memory 30 can be mounted in the endoscope device 1 and the external device, and the external memory 30 can be detached from the endoscope device 1 and the external device. In a state in which the external memory 30 is mounted in the endoscope device 1, a moving image file and a still image file are recorded in the external memory 30. Thereafter, the external memory 30 is detached from the endoscope device 1 and is mounted in the external device. The external device performs moving image reproducing processing shown in FIG. 8 or 13. When the external device can handle a still image file, the external device can use measurement correction data written in the still image file.

Since moving image reproducing processing can be performed in an external device, the endoscope device 1 need not have the function of performing moving image reproducing processing. Therefore, the control unit 103 shown in FIG. 3, the control unit 103a shown in FIG. 9, and the control unit 103b shown in FIG. 15 need not have the measurement unit 126.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope device comprising:
an endoscope insertion portion;
an adapter type determining circuit configured to determine a type of an optical adapter for measurement mounted to the endoscope insertion portion;
an image sensor configured to image a subject and generate an image of the subject; and
a processor configured to:
determine whether moving image recording processing is started; and
in response to determining that the moving image recording processing is started:
read measurement correction data corresponding to the type of the optical adapter from a first memory, the measurement correction data being data used for correcting image data corresponding to the image in measurement processing;
generate a still image file including the image data corresponding to the image when the moving image recording processing is performed;
write the measurement correction data in the still image file;
generate a moving image file including the image data corresponding to the image when the moving image recording processing is performed; and
cause the still image file in which the measurement correction data is written, and the moving image file to be associated with each other and to be recorded in a second memory,
wherein, in response to a state change from a first state to a second state, the processor is configured to generate the still image file,
wherein the first state is a state in which the optical adapter is not mounted to the endoscope insertion portion, and
wherein the second state is a state in which the optical adapter is mounted to the endoscope insertion portion, and
wherein the processor is configured to:
measure a time during which the optical adapter is mounted to the endoscope insertion portion; and
in response to the state change occurring a plurality of times, apply a filename to a plurality of still image files generated on the basis of the plurality of times of state change, the filename including the time during which the optical adapter corresponding to each still image file included in the plurality of still image files is mounted to the endoscope insertion portion.

2. The endoscope device according to claim 1, wherein the processor is configured to record the still image file in the second memory before the moving image file is generated.

3. The endoscope device according to claim 1, wherein the processor is configured to:
apply a first filename to the still image file; and
apply a second filename to the moving image file such that the first filename of the still image file in which the measurement correction data is written and the second filename of the moving image file include the same character or the same character string.

4. The endoscope device according to claim 1, wherein the processor is configured to apply the same filename to the still image file in which the measurement correction data is written and the moving image file.

5. The endoscope device according to claim 1, wherein the processor is configured to:
in response to a remaining capacity of a buffer being smaller than a capacity required to store the image data corresponding to the image when the image data corresponding to the image is to be stored in the buffer, delete at least part of image data corresponding to a previously generated image stored in the buffer;
in response to at least part of the image data corresponding to the previously generated image stored in the buffer being deleted, delete the still image file corresponding to the deleted image data corresponding to the previously generated image from the buffer;
temporarily store the image data corresponding to the image and the still image file including the image data corresponding to the image in the buffer; and
record the still image file stored in the buffer in the second memory.

6. The endoscope device according to claim 1, wherein the processor is configured to perform measurement processing on the basis of the measurement correction data which is written in the still image file recorded in the second memory, and the image data which is included in the moving image file recorded in the second memory.

7. A file recording method performed by a processor, the file recording method comprising:
determining whether moving image recording processing is started;
in response to determining that the moving image recording processing is started:
reading, from a first memory, measurement correction data corresponding to a type of an optical adapter for measurement mounted to an endoscope insertion portion,
wherein the type of the optical adapter is determined by an adapter type determination circuit,
wherein the measurement correction data is data used for correcting image data corresponding to an image of a subject in measurement processing, and
wherein the image of the subject is generated by an image sensor that images the subject;
generating a still image file including the image data corresponding to the image when the moving image recording processing is performed;
writing the measurement correction data in the still image file;
generating a moving image file including the image data corresponding to the image when the moving image recording processing is performed; and
causing the still image file in which the measurement correction data is written, and the moving image file to be associated with each other and to be recorded in a second memory;
in response to a state change from a first state to a second state, generating the still image file,
wherein the first state is a state in which the optical adapter is not mounted to the endoscope insertion portion, and
wherein the second state is a state in which the optical adapter is mounted to the endo scope insertion portion;
measuring a time during which the optical adapter is mounted to the endoscope insertion portion; and
in response to the state change occurring a plurality of times, applying a filename to a plurality of still image files generated on the basis of the plurality of times of state change, the filename including the time during which the optical adapter corresponding to each still image file included in the plurality of still image files is mounted to the endoscope insertion portion.

8. The file recording method according to claim 7, comprising:
recording the still image file in the second memory before the moving image file is generated.

9. The file recording method according to claim 7, comprising:
applying a first filename to the still image file; and
applying a second filename to the moving image file such that the first filename of the still image file in which the measurement correction data is written and the second filename of the moving image file include the same character or the same character string.

10. The file recording method according to claim 7, comprising:
applying the same filename to the still image file in which the measurement correction data is written and the moving image file.

11. The file recording method according to claim 7, comprising:
in response to a remaining capacity of a buffer being smaller than a capacity required to store the image data corresponding to the image when the image data corresponding to the image is to be stored in the buffer, deleting at least part of image data corresponding to a previously generated image stored in the buffer;
in response to at least part of the image data corresponding to the previously generated image stored in the buffer being deleted, deleting the still image file corresponding to the deleted image data corresponding to the previously generated image from the buffer;
temporarily storing the image data corresponding to the image and the still image file including the image data corresponding to the image in the buffer; and
recording the still image file stored in the buffer in the second memory.

12. The file recording method according to claim 7, comprising:
performing measurement processing on the basis of the measurement correction data which is written in the still image file recorded in the second memory, and the image data which is included in the moving image file recorded in the second memory.

13. An endoscope device comprising:
an endoscope insertion portion;
an adapter type determining circuit configured to determine a type of an optical adapter for measurement mounted to the endoscope insertion portion;
an image sensor configured to image a subject and generate an image of the subject; and
a processor configured to:
determine whether moving image recording processing is started;
in response to determining that the moving image recording processing is started:
read measurement correction data corresponding to the type of the optical adapter from a first memory, the measurement correction data being data used for correcting image data corresponding to the image in measurement processing;
generate a still image file including the image data corresponding to the image when the moving image recording processing is performed;
write the measurement correction data in the still image file;
generate a moving image file including the image data corresponding to the image when the moving image recording processing is performed; and
cause the still image file in which the measurement correction data is written, and the moving image file to be associated with each other and to be recorded in a second memory;
in response to a remaining capacity of a buffer being smaller than a capacity required to store the image data corresponding to the image when the image data corresponding to the image is to be stored in the buffer, delete at least part of image data corresponding to a previously generated image stored in the buffer;
in response to at least part of the image data corresponding to the previously generated image stored in the buffer being deleted, delete the still image file corresponding to the deleted image data corresponding to the previously generated image from the buffer;
temporarily store the image data corresponding to the image and the still image file including the image data corresponding to the image in the buffer; and
record the still image file stored in the buffer in the second memory.

14. A file recording method performed by a processor, the file recording method comprising:
determining whether moving image recording processing is started;
in response to determining that the moving image recording processing is started:
reading, from a first memory, measurement correction data corresponding to a type of an optical adapter for measurement mounted to an endoscope insertion portion,
wherein the type of the optical adapter is determined by an adapter type determination circuit,
wherein the measurement correction data is data used for correcting image data corresponding to an image of a subject in measurement processing, and
wherein the image of the subject is generated by an image sensor that images the subject;
generating a still image file including the image data corresponding to the image when the moving image recording processing is performed;
writing the measurement correction data in the still image file;
generating a moving image file including the image data corresponding to the image when the moving image recording processing is performed; and
causing the still image file in which the measurement correction data is written, and the moving image file to be associated with each other and to be recorded in a second memory;
in response to a remaining capacity of a buffer being smaller than a capacity required to store the image data corresponding to the image when the image data corresponding to the image is to be stored in the buffer, deleting at least part of image data corresponding to a previously generated image stored in the buffer;
in response to at least part of the image data corresponding to the previously generated image stored in the buffer being deleted, deleting the still image file corresponding to the deleted image data corresponding to the previously generated image from the buffer;
temporarily storing the image data corresponding to the image and the still image file including the image data corresponding to the image in the buffer; and
recording the still image file stored in the buffer in the second memory.

* * * * *